United States Patent
Pinsonneault

(10) Patent No.: US 10,978,198 B1
(45) Date of Patent: Apr. 13, 2021

(54) SYSTEMS AND METHODS FOR DETERMINING PATIENT FINANCIAL RESPONSIBILITY FOR MULTIPLE PRESCRIPTION PRODUCTS

(71) Applicant: McKesson Corporation, Irving, TX (US)

(72) Inventor: Roger G. Pinsonneault, Alpharetta, GA (US)

(73) Assignee: MCKESSON CORPORATION, Irving, TX (US)

( * ) Notice: Subject to any disclaimer, the term of this patent is extended or adjusted under 35 U.S.C. 154(b) by 106 days.

(21) Appl. No.: 16/180,915

(22) Filed: Nov. 5, 2018

Related U.S. Application Data

(63) Continuation of application No. 14/643,468, filed on Mar. 10, 2015, now Pat. No. 10,157,262.

(51) Int. Cl.
*G16H 40/20* (2018.01)

(52) U.S. Cl.
CPC .................. *G16H 40/20* (2018.01)

(58) Field of Classification Search
CPC ........ G16H 10/60; G16H 20/10; G16H 20/13; G16H 70/40; G16H 20/00; G06Q 50/22; G06Q 40/08; G06Q 50/24; G06Q 10/10; G06F 19/3456; G06F 19/328; G06F 19/3462

See application file for complete search history.

(56) References Cited

U.S. PATENT DOCUMENTS

| | | |
|---|---|---|
| 5,012,035 A | 4/1991 | Sartori et al. |
| 5,173,851 A | 12/1992 | Off et al. |

(Continued)

FOREIGN PATENT DOCUMENTS

| | | |
|---|---|---|
| CA | 2 482 370 A1 | 3/2006 |
| WO | WO 1991/006917 | 5/1991 |

(Continued)

OTHER PUBLICATIONS

United States Patent and Trademark Office, Notice of Allowance for U.S. Appl. No. 14/181,011, dated Feb. 13, 2019, 10 pages.

(Continued)

*Primary Examiner* — Joseph D Burgess
(74) *Attorney, Agent, or Firm* — Alston & Bird LLP

(57) ABSTRACT

Systems and methods are provided for determining patient financial responsibility for multiple prescription products across multiple healthcare transactions. A service provider computer can receive multiple healthcare transactions, and can evaluate each to determine if it includes a total group transaction number and a transaction number. The service provider computer can compare the transaction number to the total group transaction number to determine if all transactions within a group have been received. Once received, the transactions can be transmitted to the claims processor computer for adjudication. Upon receiving the adjudicated response for each transaction within the group, the service provider computer can identify the patient co-pay for each of the adjudicated responses in the group and can calculate a total patient pay amount based on the group of patient co-pays. The total patient pay amount may then be transmitted to a healthcare provider computer associated with a healthcare provider.

20 Claims, 5 Drawing Sheets

(56) References Cited

U.S. PATENT DOCUMENTS

| | | | |
|---|---|---|---|
| 5,628,530 A | 5/1997 | Thornton | |
| 5,595,342 A | 12/1997 | McNair et al. | |
| 5,726,092 A | 3/1998 | Mathews et al. | |
| 5,757,898 A | 5/1998 | Nishikawa | |
| 5,769,228 A | 6/1998 | Wroblewski | |
| 6,012,035 A | 1/2000 | Freeman et al. | |
| 6,111,218 A | 8/2000 | Akers et al. | |
| 6,595,342 B1 | 7/2003 | Maritzen et al. | |
| 6,726,092 B2 | 4/2004 | Goldberg et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,192,741 B2 | 3/2007 | Otte et al. | |
| 7,337,129 B1 | 2/2008 | Lowry et al. | |
| 7,346,768 B2 | 3/2008 | DiRienzo | |
| 7,409,632 B1 | 8/2008 | DiRienzo | |
| 7,734,483 B1 | 6/2010 | Smith et al. | |
| 7,783,383 B2 | 8/2010 | Eliuk et al. | |
| 7,840,424 B2 | 11/2010 | Wiley et al. | |
| 7,856,364 B1 | 12/2010 | Wiley et al. | |
| 7,912,741 B1 | 3/2011 | Pinsonneault | |
| 7,921,021 B1 | 4/2011 | Newman | |
| 8,036,913 B1* | 10/2011 | Pinsonneault | G06F 19/328 |
| | | | 705/2 |
| 8,036,918 B1 | 10/2011 | Pinsonneault | |
| 8,050,943 B1 | 11/2011 | Wiley et al. | |
| 8,060,379 B1 | 11/2011 | Pinsonneault et al. | |
| 8,326,773 B1 | 12/2012 | Bellamy | |
| 8,489,415 B1 | 7/2013 | Ringold | |
| 8,521,557 B1 | 8/2013 | Ringold et al. | |
| 8,560,340 B1 | 10/2013 | Ringold | |
| 2002/0002495 A1 | 1/2002 | Ullman | |
| 2002/0032582 A1 | 3/2002 | Feeney et al. | |
| 2002/0032583 A1 | 3/2002 | Joao | |
| 2002/0035484 A1 | 3/2002 | McCormick | |
| 2002/0087583 A1 | 7/2002 | Morgan et al. | |
| 2002/0111832 A1 | 8/2002 | Judge | |
| 2002/0147614 A1 | 10/2002 | Doerr et al. | |
| 2002/0198831 A1 | 12/2002 | Patricelli et al. | |
| 2003/0009367 A1 | 1/2003 | Morrison | |
| 2003/0050796 A1 | 3/2003 | Baldwin | |
| 2003/0050799 A1 | 3/2003 | Jay et al. | |
| 2003/0069760 A1 | 4/2003 | Gelber | |
| 2003/0074234 A1 | 4/2003 | Stasny | |
| 2003/0097310 A1 | 5/2003 | Ono et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0073456 A1 | 4/2004 | Gottlieb et al. | |
| 2004/0073457 A1 | 4/2004 | Kalies | |
| 2004/0078222 A1 | 4/2004 | Khan et al. | |
| 2004/0078234 A1 | 4/2004 | Tallal, Jr. | |
| 2004/0088187 A1 | 5/2004 | Chudy et al. | |
| 2004/0103062 A1 | 5/2004 | Wood et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0199545 A1 | 10/2004 | Wagner et al. | |
| 2004/0236630 A1 | 11/2004 | Kost et al. | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0075932 A1 | 4/2005 | Mankoff | |
| 2005/0080692 A1 | 4/2005 | Padam et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240442 A1 | 10/2005 | Lapsker et al. | |
| 2005/0240473 A1 | 10/2005 | Ayers, Jr. et al. | |
| 2005/0261939 A1 | 11/2005 | Augspurger et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0036470 A1 | 2/2006 | Oaks | |
| 2006/0085231 A1 | 4/2006 | Brofman | |
| 2006/0113376 A1 | 6/2006 | Reed et al. | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0212318 A1 | 9/2006 | Dooley | |
| 2006/0212345 A1 | 9/2006 | Soza et al. | |
| 2006/0224443 A1 | 10/2006 | Soza et al. | |
| 2006/0235747 A1 | 10/2006 | Hammond et al. | |
| 2006/0259363 A1 | 11/2006 | Jhetam et al. | |
| 2007/0005402 A1 | 1/2007 | Kennedy et al. | |
| 2007/0043589 A1 | 2/2007 | Warren et al. | |
| 2007/0050209 A1 | 3/2007 | Yered | |
| 2007/0067186 A1 | 3/2007 | Brenner et al. | |
| 2007/0094133 A1 | 4/2007 | Anandarao et al. | |
| 2007/0136100 A1 | 6/2007 | Daugherty et al. | |
| 2007/0162303 A1 | 7/2007 | Wiley et al. | |
| 2007/0185799 A1 | 8/2007 | Harrison et al. | |
| 2007/0191985 A1* | 8/2007 | Bain | G07F 9/026 |
| | | | 700/232 |
| 2007/0219813 A1 | 9/2007 | Moore | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0250341 A1 | 10/2007 | Howe et al. | |
| 2007/0276697 A1 | 11/2007 | Wiley et al. | |
| 2008/0033750 A1 | 2/2008 | Swiss et al. | |
| 2009/0030719 A1 | 1/2009 | Nadas et al. | |
| 2009/0094051 A1 | 4/2009 | Ard et al. | |
| 2009/0112707 A1 | 4/2009 | Weiss et al. | |
| 2009/0204477 A1 | 8/2009 | Urso | |
| 2009/0287558 A1 | 11/2009 | Seth et al. | |
| 2009/0313112 A1 | 12/2009 | Champ et al. | |
| 2009/0327363 A1 | 12/2009 | Cullen et al. | |
| 2010/0030667 A1 | 2/2010 | Chudy et al. | |
| 2010/0070298 A1 | 3/2010 | Kalies | |
| 2010/0144259 A1 | 6/2010 | Allexon et al. | |
| 2010/0217622 A1 | 8/2010 | Brown et al. | |
| 2010/0285821 A1 | 11/2010 | Smeeding et al. | |
| 2011/0161109 A1 | 6/2011 | Pinsonneault et al. | |
| 2011/0196697 A1 | 8/2011 | Akers | |
| 2012/0136809 A1 | 5/2012 | Cannata et al. | |
| 2012/0143627 A1* | 6/2012 | Ruben | G16H 20/10 |
| | | | 705/3 |
| 2012/0166268 A1 | 6/2012 | Griffiths | |
| 2012/0185263 A1 | 7/2012 | Emert | |
| 2012/0185264 A1 | 7/2012 | Demogenes et al. | |
| 2012/0265591 A1 | 10/2012 | Hwang | |
| 2013/0197980 A1 | 8/2013 | Lerner et al. | |
| 2013/0246082 A1 | 9/2013 | Brylawski et al. | |
| 2014/0088985 A1 | 3/2014 | Grant et al. | |
| 2014/0214435 A1 | 7/2014 | Previdi | |
| 2014/0249861 A1 | 9/2014 | Gamble et al. | |
| 2014/0278456 A1 | 9/2014 | Milosevich et al. | |
| 2015/0234991 A1 | 8/2015 | Pinsonneault | |
| 2015/0269695 A1 | 9/2015 | Pinsonneault et al. | |
| 2016/0358142 A1 | 12/2016 | Hillen | |
| 2018/0366810 A1 | 12/2018 | Nero et al. | |

FOREIGN PATENT DOCUMENTS

| | | |
|---|---|---|
| WO | WO 1995/003569 A2 | 2/1995 |
| WO | WO 1997/025682 | 7/1997 |
| WO | WO 1998/050871 | 11/1998 |
| WO | WO 2000/039737 A1 | 7/2000 |
| WO | WO 3098401 | 11/2003 |
| WO | WO 2007/025295 A2 | 3/2007 |
| WO | WO 2008/092109 | 7/2008 |

OTHER PUBLICATIONS

United States Patent and Trademark Office, Notice of Allowance for U.S. Appl. No. 14/643,468, dated Oct. 24, 2018, 22 pages.
Office Action for U.S. Appl. No. 15/085,166 dated Mar. 3, 2020.
Office Action for U.S. Appl. No. 15/085,166 dated Dec. 27, 2018.
Office Action for U.S. Appl. No. 14/229,043 dated Feb. 27, 2019.
U.S. Appl. No. 14/229,043, filed Mar. 28, 2014, Pinsonneault.

(56) References Cited

OTHER PUBLICATIONS

U.S. Appl. No. 15/085,166, filed Mar. 30, 2016, Kaye et al.
Office Action for U.S. Appl. No. 15/085,166 dated Sep. 4, 2019 23 pages.
Office Action for U.S. Appl. No. 14/229,043 dated Sep. 5, 2019.
Notice of Allowance for U.S. Appl. No. 14/181,011 dated May 15, 2019.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Consalvo, Bob; "City of Bosont in the City Council" hearing notice, Dec. 6, 2006.
Coping with Information Overload. The News Source for Healthcare Information Technology [Online] Nov. 2004. URL: http://www.awarix.com.
Final Office Action for U.S. Appl. No. 12/140,015 dated Jan. 31, 2011.
Final Office Action for U.S. Appl. No. 12/415,062 dated Oct. 6, 2011.
Final Office Action for U.S. Appl. No. 12/555,589 dated Apr. 11, 2012.
Final Office Action for U.S. Appl. No. 12/560,071 dated Aug. 28, 2015.
Final Office Action for U.S. Appl. No. 12/560,071 dated Nov. 8, 2012.
Final Office Action for U.S. Appl. No. 12/570,982 dated Apr. 11, 2014.
Final Office Action for U.S. Appl. No. 12/570,982 dated Aug. 28, 2015.
Final Office Action for U.S. Appl. No. 12/570,982 dated Jan. 17, 2013.
Final Office Action for U.S. Appl. No. 12/730,015 dated Aug. 14, 2012.
Final Office Action for U.S. Appl. No. 12/978,898 dated May 16, 2013.
Final Office Action for U.S. Appl. No. 13/721,890 dated Jun. 24, 2015.
Final Office Action for U.S. Appl. No. 13/721,890 dated Nov. 25, 2016.
Final Office Action for U.S. Appl. No. 13/782,909 dated May 31, 2016.
Final Office Action for U.S. Appl. No. 13/782,909 dated Oct. 6, 2015.
Final Office Action for U.S. Appl. No. 13/804,175 dated Oct. 6, 2015.
Final Office Action for U.S. Appl. No. 14/090,113 dated Jan. 6, 2016.
Final Office Action for U.S. Appl. No. 14/090,122 dated Apr. 22, 2016.
Final Office Action for U.S. Appl. No. 14/193,294 dated May 2, 2016.
Final Office Action for U.S. Appl. No. 14/218,326 dated Jun. 30, 2016.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 dated Jan. 14, 2015.
Marie Chisholm et al. "Pharmaceutical Manufacturer Assistance Program." Arch Intern Med. vol. 162, Apr. 8, 2002.
Non-Anal Office Action for U.S. Appl. No. 13/721,890 dated Jun. 14, 2016.
Non-Final Office Action for U.S. Appl. No. 12/560,071 dated Jun. 21, 2012.
Non-Final Office Action for U.S. Appl. No. 12/570,982 dated Jun. 20, 2012.
Non-Final Office Action for U.S. Appl. No. 14/193,294 dated Feb. 21, 2017.
Non-final Office Action for U.S. Appl. No. 12/140,015 dated Oct. 8, 2010.
Non-final Office Action for U.S. Appl. No. 12/189,650 dated Jan. 22, 2010.
Non-final Office Action for U.S. Appl. No. 12/189,654 dated Jan. 22, 2010.
Non-Final Office Action for U.S. Appl. No. 12/415,062 dated Mar. 30, 2011.
Non-Final Office Action for U.S. Appl. No. 12/555,589 dated Dec. 9, 2011.
Non-Final Office Action for U.S. Appl. No. 12/560,071 dated Sep. 23, 2014.
Non-Final Office Action for U.S. Appl. No. 12/570,982 dated Sep. 12, 2013.
Non-Final Office Action for U.S. Appl. No. 12/730,015 dated Mar. 6, 2012.
Non-Final Office Action for U.S. Appl. No. 12/956,411 dated Jan. 24, 2011.
Non-Final Office Action for U.S. Appl. No. 12/978,898 dated Feb. 6, 2013.
Non-Final Office Action for U.S. Appl. No. 12/982,395 dated Dec. 11, 2012.
Non-Final Office Action for U.S. Appl. No. 13/721,890 dated Jan. 9, 2015.
Non-final Office Action for U.S. Appl. No. 13/782,909 dated Feb. 11, 2016.
Notice of Allowance for U.S. Appl. No. 11/674,069 dated Jul. 19, 2010.
Notice of Allowance for U.S. Appl. No. 12/140,015 dated Jun. 10, 2011.
Notice of Allowance for U.S. Appl. No. 12/165,221 dated Nov. 16, 2010.
Notice of Allowance for U.S. Appl. No. 12/189,650 dated Aug. 13, 2010.
Notice of Allowance for U.S. Appl. No. 12/956,411 dated Aug. 5, 2011.
Notice of Allowance for U.S. Appl. No. 12/982,395 dated Apr. 24, 2013.
Office Action for U.S. Appl. No. 12/570,982 dated Apr. 8, 2015.
Office Action for U.S. Appl. No. 14/181,011 dated Feb. 29, 2016.
Office Action for U.S. Appl. No. 14/181,011 dated Mar. 20, 2017.
Office Action for U.S. Appl. No. 14/181,011 dated Oct. 20, 2016.
Office Action for U.S. Appl. No. 14/181,011 dated Sep. 12, 2017.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/229,043 dated Jul. 24, 2017.
Office Action for U.S. Appl. No. 14/643,468 dated Mar. 8, 2018.
Office Action for U.S. Appl. No. 15/085,166 dated Jun. 29, 2018 19 pages.
Office Action for U.S. Appl. No. 13/782,909 dated Jun. 25, 2015.
Office Action for U.S. Appl. No. 13/804,175 dated Mar. 13, 2015.
Office Action for U.S. Appl. No. 14/090,122 dated Oct. 21, 2016.
Office Action for U.S. Appl. No. 14/090,122 dated Sep. 11, 2015.
Office Action for U.S. Appl. No. 14/1090,113 dated Jun. 18, 2015.

(56) References Cited

OTHER PUBLICATIONS

Office Action for U.S. Appl. No. 14/1218,326 dated Dec. 1, 2015.
Office Action for U.S. Appl. No. 14/193,294 dated Dec. 17, 2015.
Opar, Alisa; "Rising drug costs prompt new uses for old pills." Nature Medicine, 1211333 (2006).
Pharmacy Reject Codes NCPDP.
Sampson, R.J., Taking Control of Health Care Costs, Best's Review—Life Health Insurance Edition, Nov. 1983, vol. 84, Issue 7, USA; Abstract only.
Siller et al., "Safe Disposal of Unused Controlled Substances" Avalere Health 2008.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Strom, Stephanie; "Old Pills Finding New Medicine Cabinets" NY Times, May 18, 2005.
Subnotebooks,Phones, and More. St. Vincent's Gets on Track. Mobile Health Data [Online], Nov. 19, 2004. URL:http://www.awarix.com.
Two automatic identification technology, neither new in the sense if being recent developments . . . Patient Safety & Quality Healthcare [Online] Aug. 2005_ URL: http://www_awarix.com.
Wisconsin Physicians Service (WPS) Insurance Corporation, "How to Read Your Explanation of Benefits Chart," Jun. 16, 2012.
www.ncoil.org/news/DrugCards2.doc dated Apr. 2002.
Office Action for U.S. Appl. No. 14/229,043 dated Sep. 14, 2018.
Non-Final Office Action for U.S. Appl. No. 15/085,166 dated Jun. 12, 2020, 40 pages.
Final Office Action for U.S. Appl. No. 15/085,166 dated Dec. 4, 2020, 12 pages.
Advisory Action received for U.S. Appl. No. 15/085,166, dated Jan. 29, 2021, 5 pages.

\* cited by examiner

SYSTEMS AND METHODS FOR DETERMINING PATIENT FINANCIAL RESPONSIBILITY FOR MULTIPLE PRESCRIPTION PRODUCTS

CROSS REFERENCE TO RELATED APPLICATIONS

This application is a continuation of U.S. application Ser. No. 14/643,468 filed Mar. 10, 2015, the entire contents of which are incorporated herein by reference.

TECHNICAL FIELD

Aspects of the disclosure relate generally to a determination of financial responsibility for products, and more particularly, to systems and methods for determining a patient's total financial responsibility when receiving multiple disparate prescription products at a time.

BACKGROUND

Over the past several years, healthcare plans offered by insurance companies and government-sponsored insurers (collectively referred to herein as insurers) have become exceedingly more complex. This includes situations where a patient may be trying to fill a prescription for a medication or other product. Instead of simply covering the cost of the prescription product, these insurers may require a co-pay from the patient. The co-pay may also be different for certain types of products (e.g., name brand products versus generics). In addition, the insurers may have a deductible that has to be met by the patient and/or the patient's family before the insurer covers the prescription product or covers a greater amount of the prescription product. Furthermore, the insurer may cover some products while denying coverage for other products. Finally, each insurer may have a one or more different sets of rules, co-pay levels, deductible levels, and product coverage groupings depending on the type of coverage being provided to the specific patient.

All of this makes it exceedingly difficult for pharmacists as well as prescribers of medication (e.g., doctors, nurses, nurse-practitioners, or any other person legally permitted to prescribe medication) to know ahead of time what it may cost a patient when products are being prescribed. However, this cost information can be vitally important to provide to the patient ahead of time to help determine the likelihood that the patient will fill all of the prescriptions and be provided the necessary benefit of each prescribed product.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods that facilitate the determination of patient financial responsibility for multiple prescription products, as part of the processing of the healthcare transaction in real-time or near real-time. For example, a pharmacist or a physician or other prescriber (e.g., nurse, physician's assistant, hospital, doctor's office, or any other person legally permitted to prescribe a medication) can electronically transmit multiple healthcare transactions, such as a predetermination of benefits transaction, healthcare claim transaction, prescription claim or billing request, healthcare order transaction, or e-prescription transaction (e.g., electronic prescription order transaction, e-script, or e-prescription) for the patient to a service provider computer. Each healthcare transaction may include patient information identifying the patient, medication/product information identifying the prescribed product, a transaction number, and a total group transaction count (e.g., 1 of 6, 2 of 6, etc.). The service provider computer can evaluate the healthcare transaction to determine transaction number and total group transaction count identified in the healthcare transaction. The service provider computer may further determine if the transaction number equals the total group transaction count. In certain embodiments, once the transaction number equals the total group transaction count, the service provider computer may transaction each individual healthcare transaction that makes up the total group transaction count to a claims processor computer for adjudication.

Figure 1:
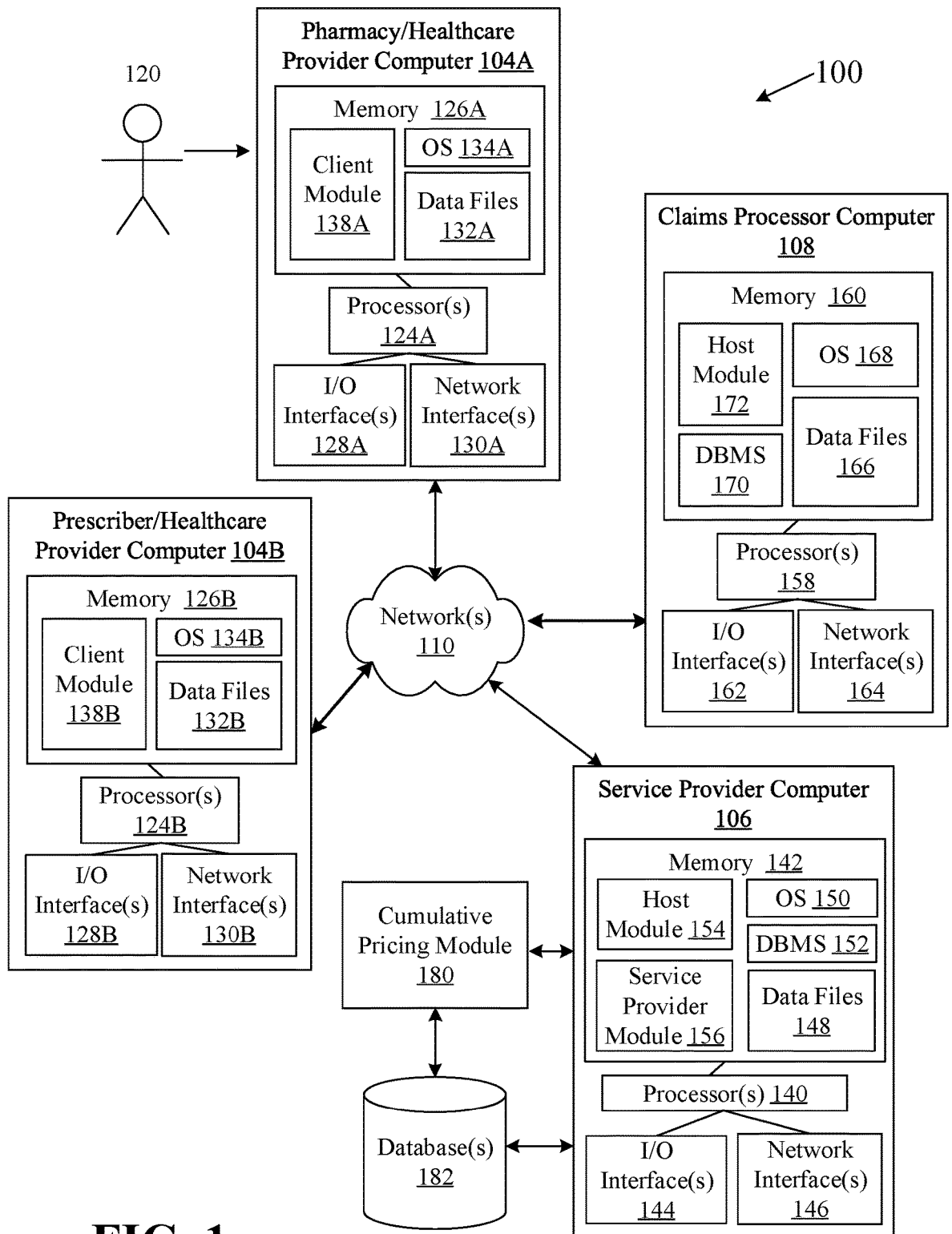
FIG. 1 illustrates an example overview of a system that facilitates determining patient financial responsibility for multiple prescription products, according to one exemplary embodiment of the disclosure.

Once each of the healthcare transactions in the group have been adjudicated, the service provider computer may receive each adjudicated response for each of the healthcare transactions in the group from the claims processor computer. The service provider computer may identify the patient pay amount in each of the adjudicated responses in the group and may further calculate, based on each individual patient pay amount, a total patient pay amount that covers all of the healthcare transactions in the group. The service provider computer may transmit the adjudicated response for each healthcare transaction in the group along with the total patient pay amount calculated to the healthcare provider computer from which the healthcare transactions originated. The total patient pay amount may be included in a message appended to one or more of the adjudicated responses to the healthcare transactions. Further, the service provider computer may automatically and without receiving a request from the healthcare provider computer, transmit reversal transactions to the claims processor computer for each of the healthcare transactions System Overview FIG. 1 illustrates an example system 100 supporting healthcare transactions, electronic prescription ordering activities, prescription billing activities, and patient coverage eligibility verifications according to one example embodiment. The exemplary system 100 facilitates determining patient financial responsibility for multiple prescription products as part of the processing of the healthcare transaction, including, but not limited to, an eligibility verification request, predetermination of benefits transaction, healthcare claim transaction, prescription claim or billing request, healthcare order transaction, or e-prescription transaction (e.g., electronic prescription order transaction, e-script, or e-prescription), and will now be described illustratively with respect to FIG. 1. As shown in FIG. 1, the system 100 may include at least one healthcare provider computer 104, at least one service provider computer 106, and at least one claims processor computer 108. As shown in FIG. 1, multiple healthcare provider computers 104A and 104B are presented by way of example and may be referred to individually or collectively as "healthcare provider computer 104" hereinafter. Alternatively, each of the pharmacy/healthcare provider computer 104A and prescriber/healthcare provider computer 104B may be specifically discussed with reference to designations on FIG. 1.

As desired, each of the healthcare provider computers 104A and 104B, service provider computer 106, and/or claims processor computer 108 may include one or more processing devices that may be configured for accessing and reading associated computer-readable media having stored thereon data and/or computer-executable instructions for implementing various methods, including those described herein.

Additionally, in certain exemplary embodiments, the service provider computer 106 may be in communication with one or more cumulative pricing modules 180, which may access and/or be in communication with one or more suitable data storage devices, such as database 182. The cumulative pricing module 180 may receive healthcare transactions or all or a portion of the data from healthcare transactions from the service provider computer 106. Upon receipt of the healthcare transaction data, the cumulative pricing module 180 may evaluate the data to determine if multiple healthcare transactions are being submitted for a patient (e.g., via a total group transaction count or other group transaction identifier) and the transaction number for the current healthcare transaction as part of that group. The cumulative pricing module 180 may compare the transaction number of the current healthcare transaction to the total group transaction count to determine if all of the transactions in the group have been received. Once received, the cumulative pricing module 180 can facilitate the transmission of each healthcare transaction in the group of healthcare transactions to one or more claims processor computers 108 via the service provider computer 106 for adjudication.

Upon receipt of the adjudicated response for each of the healthcare transactions in the group of healthcare transactions, the cumulative pricing module 180 may retrieve the patient pay amount (e.g., patient co-pay) from each of the adjudicated responses in the group and can calculate the total patient pay amount based on the retrieved patient pay amounts from each adjudicated response. The cumulative pricing module 180 may generate a message or append a message to one or more of the adjudicated responses for the group of healthcare transactions. The message may include the total patient pay amount for the prescribed products in the group of healthcare transactions. The adjudicated response for each of the healthcare transactions in the group of healthcare transactions may be transmitted from the service provider computer to the healthcare provider computer 104 from which the healthcare transactions originated. The cumulative pricing module 180 may automatically, and without receiving a request from the healthcare provider computer 104, generate a reversal transaction for each of the healthcare transactions in the group of healthcare transactions. The cumulative pricing module 180 may facilitate the transmission of the group of reversal transactions from the service provider computer 106 to the one or more claims processors 108. While FIG. 1 shows the cumulative pricing module 180 as being separate from the service provider computer 106, in certain example embodiments, the cumulative pricing module 180 is part of the service provider computer 106 and sending and receiving between the two are internal transmissions within the service provider computer 106. Furthermore, while FIG. 1 shows the cumulative pricing module 180 as a single module, in certain example embodiments, the functions/operations discussed below with regard to the cumulative pricing module 180 may be completed by multiple modules, all or a portion of which may be part of the service provider computer 106.

Generally, network devices and systems, including one or more of the healthcare provider computers 104A and 104B, service provider computer 106, cumulative pricing module 180, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computers 104A and 104B, service provider computer 106, claims processor computer 108, and cumulative pricing module 180 may be in communication with each other via one or more networks, such as network 110, which as described below can include one or more separate or shared private and public networks, including the Internet or a publicly switched telephone network. Each of these components—the healthcare provider computers 104A and 104B, service provider computer 106, claims processor computer 108, cumulative pricing module 180, and the network 110 will now be discussed in further detail.

Each healthcare provider computer 104 may be associated with a healthcare provider, such as, for example, a pharmacy, physician's office, hospital, clinic, hospice, etc. While the exemplary healthcare provider computers 104A and 104B reference and can be located within a pharmacy (104A) and an office for a prescriber (104B) this is for example only and is not intended to be limiting in any manner. Each healthcare provider computer 104A and 104B may be any suitable processor-driven device that facilitates the processing of healthcare requests made by patients, consumers, or prescribers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain example embodiments, each healthcare provider computer 104A and 104B may be a suitable point of sale device associated with a healthcare provider. The execution of the computer-implemented instructions by either healthcare provider computer 104A or 104B may form a special purpose computer or other particular machine that is operable to facilitate the processing of healthcare requests made by patients and the communication of healthcare transactions to a service provider computer 106. Additionally, in certain example embodiments of the disclosure, the operations and/or control of each healthcare provider computer 104A and 104B may be distributed amongst several processing components.

In addition to each healthcare provider computer 104A and 104B having one or more processors 124A and 124B, each healthcare provider computer 104A and 104B may also include one or more memory devices 126A and 126B, one or more input/output ("I/O") interfaces 128A and 128B, and one or more network interfaces 130A and 130B. The memory devices 126A and 126B may be any suitable memory device, for example, caches, read-only memory devices, random access memory devices, magnetic storage devices, removable storage devices, etc. The memory devices 126A and 126B may store data, executable instructions, and/or various program modules utilized by each respective healthcare provider computer 104A and 104B, for example, data files 132A and 132B, an operating system ("OS") 134A and 134B, and/or a client module 138A and 138B, respectively. Each of the data files 132A and 132B may include any suitable data that facilitates the receipt and/or processing of healthcare requests by the respective healthcare provider computer 104A and 104B and the generation and/or processing of healthcare transactions that are communicated to the service provider computer 106. For example, the data files 132A and 132B may include, but are not limited to, healthcare information and/or contact information associated with one or more patients, information associated with the particular healthcare provider and/or the respective healthcare provider computer 104A and 104B, information associated with the service provider computer 106, information associated with one or more claims processors, and/or information associated with one or more healthcare transactions. The OS 134A and 134B may be any suitable software module that controls the general operation of the respective healthcare provider computer 104A and 104B. The OS 134A and 134B may also facilitate the execution of other software modules by the one or more respective processors 124A and 124B, for example, the client module 138A and 138B. The OS 134A and 134B may be any currently existing or future developed operating system include, but not limited to, Microsoft Windows®, Apple OSX™, Linux, Unix, or a mainframe operating system.

Each client module 138A and 138B may be, for example, an Internet browser or other suitable software, including a dedicated program, for interacting with the service provider computer 106. For example, a user 120, such as a pharmacist, pharmacy assistant, nurse practitioner, physician, nurse, or other pharmacy, hospital or physician's office employee, may utilize the respective client module 138A and 138B in preparing and providing a healthcare transaction, such as a predetermination of benefits request, healthcare claim transaction, prescription claim or billing request, healthcare order transaction, or e-prescription transaction (e.g., electronic prescription order transaction, e-script, or e-prescription), to the service provider computer 106 for delivery to: i) the appropriate claims processor computer 108 or other third-party for adjudication or other coverage/benefits determination, or ii) the appropriate other healthcare provider computer, such as from the prescriber/healthcare provider computer 104B to a pharmacy/healthcare provider computer 104A for dispensing of the prescribed medication. Each healthcare provider computer 104A and 104B may also utilize the respective client module 138A and 138B to retrieve or otherwise receive data, messages, or responses from the service provider computer 106 and/or other components of the system 100. For example, in certain example embodiments, the client module 138A and 138B may be utilized to receive a healthcare transaction, a rejection of the healthcare transaction, a prescription fill status notification, and/or an adjudicated response to the healthcare transaction from the service provider computer 106 as will be described below.

The one or more I/O interfaces 128A and 128B may facilitate communication between the respective healthcare provider computer 104A and 104B and one or more input/output devices, for example, one or more user interface devices, such as, a keyboard, mouse, display, keypad, control panel, touch-screen display, remote control, microphone, etc., that facilitate user interaction with the particular healthcare provider computer 104A and 104B. For example, the one or more I/O interfaces 128A and 128B may facilitate entry of information associated with a healthcare transaction by an employee 120 of a healthcare provider, such as a pharmacy employee, pharmacist, physician, nurse, hospital employee, nurse practitioner, or the like affiliated with a pharmacy, hospital, physician's office, clinic, or other similar healthcare provider. The one or more network interfaces 130A and 130B may facilitate connection of the particular healthcare provider computer 104A and 104B to one or more suitable networks, for example, the network 110 illustrated in FIG. 1. In this regard, each healthcare provider computer 104A and 104B may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the healthcare provider computers 104A and/or 104B, the cumulative pricing module 180, and/or the claims processor computer 108 relating to pharmacy benefits, billing, electronic prescription submission, and/or other healthcare transactions and/or other activities. In certain exemplary embodiments, the service provider computer 106 may be a switch/router that routes healthcare transactions and/or other healthcare requests from healthcare provider computers 104 to the correct one of many claims processor computers 108. For example, the service provider computer 106 may route healthcare transactions communicated from one of the healthcare provider computers 104A and 104B to a claims processor computer 108, such as a pharmacy benefits manager (PBM), an insurer, a Medicare payor, a Medicare Part D payor, accountable care organization, or other third-party payor. In another example, the service provider computer 106 may route healthcare transactions communicated from a prescriber/healthcare provider computer 104B (or other prescriber of medication, products, and/or services) to the pharmacy/healthcare provider computer 104A.

In certain example embodiments, the service provider computer 106 may include a suitable host server, host module 154, or other software that facilitates the receipt of a healthcare transaction from a healthcare provider computer 104A and 104B and/or the routing of the received healthcare transaction to a claims processor computer 108 or pharmacy/healthcare provider computer 104A. Any number of healthcare provider computers 104A and 104B, cumulative pricing modules 180, and/or claims processor computers 108 may be in communication with the service provider computer 106 as desired in various embodiments.

The service provider computer 106 may include any number of special purpose computers or other particular machines, application-specific circuits, microcontrollers, personal computers, minicomputers, mainframe computers, servers, networked computers, and/or other processor-driven devices. In certain example embodiments, the operations of the service provider computer 106 may be controlled by computer-executed or computer-implemented instructions that are executed by one or more processors associated with the service provider computer 106 to form a special-purpose computer or other particular machine that is operable to facilitate the receipt, routing, and/or processing of healthcare transactions. The one or more processors that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the healthcare provider computers 104A and 104B described above, the service provider computer 106 may include one or more processors 140, one or more memory devices 142, one or more input/output ("I/O") interface(s) 144, and one or more network interface(s) 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider 106, for example, data files 148, an operating system ("OS") 150, the host module 154, a service provider module 156, and a database management system ("DBMS") 152 to facilitate management of data files 148 and other data stored in the memory devices 142. The OS 150 may be any currently existing or future-developed operating system including, but not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The service provider module 156 may be operable to perform one or more pre-edits or pre-analysis on a received healthcare transaction prior to routing or otherwise communicating the received healthcare transaction, such as a healthcare claim transaction, to a suitable claims processor computer 108 or an e-prescription transaction to a suitable pharmacy/healthcare provider computer 104A. Additionally, the service provider module 156 may be operable to perform one or more post-edits on an adjudicated reply or response that is received from a claims processor computer 108 for a healthcare transaction prior to routing the adjudicated response to one of the healthcare provider computers 104A and 104B. In certain example embodiments, the service provider module 156 may also be operable to perform the functions described with references to the cumulative pricing module 180 herein. A wide variety of different pre-edits and/or post-edits may be performed by the service provider module 156 as desired in various embodiments of the disclosure.

According to one exemplary embodiment, the data files 148 may store healthcare transaction records associated with communications received from various healthcare provider computers 104A and 104B, the cumulative pricing module 180, and/or various claims processor computers 108. The data files 148 may also store any number of suitable routing tables that facilitate determining the destination of communications received from a healthcare provider computer 104A and 104B, the cumulative pricing module 180, and/or the claims processor computer 108.

The exemplary data files 148 may also store records containing, for example, tables, schedules, or lists of patient identification data (e.g., patient first name, patient last name, patient social security number or healthcare insurance claim number (HICN number), cardholder ID and/or person code for the patient) and medication/product identification data (e.g., National Drug Code (NDC code) medication/product name and/or other medication/product identifier) for patients, healthcare transactions received for the patient, an identification of whether the healthcare transaction is part of a group of healthcare transactions, and if so, a total group transaction count and a transaction number for the healthcare transaction, as well as patient co-pay amount for each transaction in the group of healthcare transactions and a total patient pay amount (if adjudications for each transaction in the group of healthcare transactions has been received from the respective one or more claims processor computers 108).

The host module 154 may receive, process, and respond to requests from the client module 138 of one of the healthcare provider computers 104A and 104B, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware, or software without departing from exemplary embodiments disclosed herein.

With continued reference to the service provider computer 106, the one or more I/O interfaces 144 may facilitate communication between the service provider computer 106 and one or more input/output devices, for example, one or more user interface devices, such as a keyboard, mouse, display, keypad, control panel, touch-screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

The cumulative pricing module 180 of FIG. 1 represents one or more modules that can evaluate a healthcare transaction or data from a healthcare transaction to determine if the transaction is one of a group of transactions or the transaction includes multiple requests for prescription medication, can determine the transaction number for the healthcare transaction as part of the group of healthcare transactions, can facility adjudication of each of the transactions in the group of healthcare transactions, can determine the patient co-pay amount in each of the adjudicated responses to each of the transactions in the group of healthcare transactions; can calculate a total patient pay amount for the prescribed products in the group of healthcare transactions; can generate messaging back to the healthcare provider computer 104A or 104B providing the total patient pay amount, can generate reversal transactions for each of the healthcare transactions in the group of healthcare transactions, and can facilitate the transmission of the reversal transactions to the one or more claims processor computers 108. The example cumulative pricing module 180 may include computer-executable instructions for receiving and processing healthcare transactions, healthcare transaction data, adjudicated responses (or data therefrom) to healthcare transactions from a service provider computer 106 or claims processor computer 108.

The cumulative pricing module 180 may receive healthcare transactions or all or a portion of the data from healthcare transactions from the service provider computer 106. Upon receipt of the healthcare transaction data, the cumulative pricing module 180 may evaluate the data to determine if multiple healthcare transactions are being submitted for a patient (e.g., via a total group transaction count or other group transaction identifier) and the transaction number for the current healthcare transaction as part of that group. The cumulative pricing module 180 may compare the transaction number of the current healthcare transaction to the total group transaction count to determine if all of the transactions in the group have been received. Once received, the cumulative pricing module 180 can facilitate the transmission of each healthcare transaction in the group of healthcare transactions to one or more claims processor computers 108 via the service provider computer 106 for adjudication.

Upon receipt of the adjudicated response for each of the healthcare transactions in the group of healthcare transactions, the cumulative pricing module 180 may retrieve the patient pay amount (e.g., patient co-pay) from each of the adjudicated responses in the group and can calculate the total patient pay amount based on the retrieved patient pay amounts from each adjudicated response. The cumulative pricing module 180 may generate a message or append a message to one or more of the adjudicated responses for the group of healthcare transactions. The message may include the total patient pay amount for the prescribed products in the group of healthcare transactions. The adjudicated response for each of the healthcare transactions in the group of healthcare transactions may be transmitted from the service provider computer to the healthcare provider computer 104 from which the healthcare transactions originated. The cumulative pricing module 180 may automatically, and without receiving a request from the healthcare provider computer 104, generate a reversal transaction for each of the healthcare transactions in the group of healthcare transactions. The cumulative pricing module 180 may facilitate the transmission of the group of reversal transactions from the service provider computer 106 to the one or more claims processors 108. While FIG. 1 shows the cumulative pricing module 180 as being separate from the service provider computer 106, in certain example embodiments, the cumulative pricing module 180 is part of the service provider computer 106 (such as being part of or separate from the service provider module 156) and sending and receiving between the two are internal transmissions within the service provider computer 106. Furthermore, while FIG. 1 shows the cumulative pricing module 180 as a single module, in certain example embodiments, the functions/operations discussed below with regard to the cumulative pricing module 180 may be completed by multiple modules, all or a portion of which may be part of the service provider computer 106.

As desired, the cumulative pricing module 180 may include any number of special purpose computers or other particular machines, application-specific circuits, microcontrollers, personal computers, minicomputers, mainframe computers, servers, and the like. In certain exemplary embodiments, the operations of the cumulative pricing module 180 may be controlled by computer-executed or computer-implemented instructions that are executed by one or more processors associated with the cumulative pricing module 180 to form a special purpose computer or other particular machine that is operable to facilitate the receipt, processing, and/or storage of healthcare transactions, healthcare transaction data, and/or adjudicated response data received from the service provider computer 106 and/or the claims processor computer 108. The one or more processors that control the operations of the cumulative pricing module 180 may be incorporated into the cumulative pricing module 180 and/or in communication with the cumulative pricing module 180 via one or more suitable networks, such as network 110. In certain example embodiments, the operations and/or control of the cumulative pricing module 180 may be distributed amongst several processing components.

Similar to other components of the system 100, the cumulative pricing module 180 may include one or more processors, one or more memory devices, one or more I/O interfaces, and one or more network interfaces. The one or more memory devices may be any suitable memory devices, for example, caches, read only memory devices, random access memory devices, magnetic storage devices, removable memory devices. The one or more memory devices may store data, executable instructions, and/or various program modules utilized by the cumulative pricing module 180, for example, data files, an OS, a DBMS, and a host module. The data files may include any suitable information that is utilized by the cumulative pricing module 180 to receive, process, analyze, and/or store healthcare transaction data and/or adjudicated response data. The OS may be a suitable software module that controls the general operation of the particular cumulative pricing module 180. The OS may also facilitate the execution of other software modules by the one or more processors, for example, the DBMS and/or the host module. The OS may be any currently existing or future-developed operating system including, but not limited to, Microsoft Windows®, Apple OSX™, Linux, Unix, or a mainframe operating system. The DBMS may be a suitable software module that facilitates access and management of one or more databases, such as database 182, that are utilized to store information that is received by or utilized by the cumulative pricing module 180 and/or the service provider computer 106. The host module may initiate, receive, process, analyze, store, and/or respond to requests, such as the receipt of healthcare transactions or healthcare transaction data from the host module 154 of the service provider computer 106. The cumulative pricing module 180 may include additional program modules as desired. Those of ordinary skill in the art will appreciate that the cumulative pricing module 180 may include alternate and/or additional components, hardware or software without departing from example embodiments disclosed herein.

The one or more I/O interfaces may facilitate communication between the cumulative pricing module 180 and one or more input/output devices, for example, one or more user interface devices, such as a keyboard, mouse, display, keypad, control panel, touch-screen display, remote control, microphone, etc. that facilitate user interaction with the cumulative pricing module 180. The one or more network interfaces may facilitate connection of cumulative pricing module 180 to one or more suitable networks, for example, the network 110 illustrated in FIG. 1. In this regard, the cumulative pricing module 180 may receive healthcare transactions, healthcare transaction data, adjudicated responses, adjudicated response data, and/or other communications from the service provider computer 106 and/or the claims processor computer 108.

The database(s) 182 may be operable to store information associated with various patients and/or various healthcare transactions including, but not limited to, tables, schedules, or lists of patient identification data (e.g., patient first name, patient last name, patient social security number or HICN number, cardholder ID and/or person code for the patient) for patients tables, schedules, or lists of medication identifiers (e.g., the related NDC code, RxNorm number, and/or medication/product name) for the one or more prescribed products/medications identified in the healthcare transaction, healthcare transactions received for the patient, an identification of whether the healthcare transaction is part of a group of healthcare transactions, and if so, a total group transaction count and a transaction number for the healthcare transaction, as well as patient co-pay amount for each transaction in the group of healthcare transactions and a total patient pay amount (if adjudications for each transaction in the group of healthcare transactions has been received from the respective one or more claims processor computers 108). The healthcare transaction, patient and prescription medication/product data in the database 182 may then be accessed and evaluated by the cumulative module 180 and/or the service provider computer 106.

With continued reference to FIG. 1, the claims processor computer 108 may be any suitable processor-driven device that facilitates receiving, processing, and/or fulfilling healthcare transactions, such as predetermination of benefits requests, healthcare claim transactions, prescription claim or billing requests, healthcare order transactions, or e-prescription transactions (e.g., electronic prescription order transactions, e-scripts, or e-prescriptions) received from the service provider computer 106 and/or the cumulative pricing module 182. For example, the claims processor computer 108 may be a processor-driven device associated with a pharmacy benefits manager (PBM), an insurer, a government payor, a Medicare Part D payor, accountable care organization, or a claims clearinghouse. As desired, the claims processor computer 108 may include any number of special purpose computers or other particular machines, application-specific circuits, microcontrollers, personal computers, minicomputers, mainframe computers, servers, and the like.

In certain exemplary embodiments, the operations of the claims processor computer 108 may be controlled by computer-executed or computer-implemented instructions that are executed by one or more processors associated with the claims processor computer 108 to form a special-purpose computer or other particular machine that is operable to facilitate the receipt, processing, and/or fulfillment of healthcare transaction requests and/or reversal transactions received from the service provider computer 106 and/or the cumulative pricing module 180. The one or more processors that control the operations of the claims processor computer 108 may be incorporated into the claims processor computer 108 and/or in communication with the claims processor computer 108 via one or more suitable networks. In certain embodiments, the operations and/or control of the claims processor computer 108 may be distributed amongst several processing components.

Similar to other components of the system 100, the claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions and/or reversal transactions, for example, patient profiles, patient insurance information (e.g., co-pay levels, deductible levels, groups of covered/uncovered products, etc.), other information associated with a patient, information associated with a healthcare provider, etc. The operating system (OS) 168 may be a suitable software module that controls the general operation of the claims processor computer 108. The OS 168 may also facilitate the execution of other software modules by the one or more processors 158, for example, the DBMS 170 and/or the host module 172. The OS 168 may be any currently existing or future-developed operating system including, but not limited to, Microsoft Windows®, Apple OSX™, Linux, Unix, or a mainframe operating system.

The DBMS 170 may be a suitable software module that facilitates access and management of one or more databases that are utilized to store information that is utilized by the claims processor computer 108 in various example embodiments of the disclosure. The host module 172 may initiate, receive, process, and/or respond to requests, such as healthcare transactions, reversal transactions, or claim requests, from the host module 154 of the service provider 106. The claims processor computer 108 may include additional program modules for performing other pre-processing or post-processing methods described herein. Those of ordinary skill in the art will appreciate that the claims processor computer 108 may include alternate and/or additional components, hardware or software without departing from the example embodiments described herein.

The one or more I/O interfaces 162 may facilitate communication between the claims processor computer 108 and one or more input/output devices, for example, one or more user interface devices, such as a keyboard, mouse, display, keypad, control panel, touch-screen display, remote control, microphone, etc. that facilitate user interaction with the claims processor computer 108. The one or more network interfaces 164 may facilitate connection of the claims processor computer 108 to one or more suitable networks, for example, the network 110. In this regard, the claims processor computer 108 may receive healthcare transactions, reversal transactions, and/or other communications from the service provider computer 106 and/or the cumulative pricing module, and the claims processor computer 108 may communicate information associated with processing the healthcare transactions and/or reversal transactions to the service provider computer 106 and/or the cumulative pricing module.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computers 104A and 104B, the service provider computer 106, cumulative pricing module 180, and/or the claims processor computer 108. Due to network connectivity, various methodologies, as described herein may be practiced in the context of distributed computing environments. Although the service provider computer 106 is shown for simplicity as being in communication with the healthcare provider computers 104A and 104B, the cumulative pricing module 180, or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 106 may form the basis of network 110 that interconnects one or more of the healthcare provider computers 104A and 104B, the cumulative pricing module 180, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 106 (or other computer) may be implemented as a specialized processing machine that includes hardware and/or software for performing the methods described herein. In addition, at least a portion of the processor and/or processing capabilities of the service provider computer 106 may be implemented as part of the claims processor computer 108 or the healthcare provider computer 104. In addition, at least a portion of the processor and/or processing capabilities of the healthcare provider computer 104, and/or the claims processor computer 108 may be implemented as part of the service provider computer 106. Accordingly, the exemplary embodiments described herein should not be construed as being limited to any particular operating environment, system architecture, or device configuration.

Operational Overview

Figure 2A:
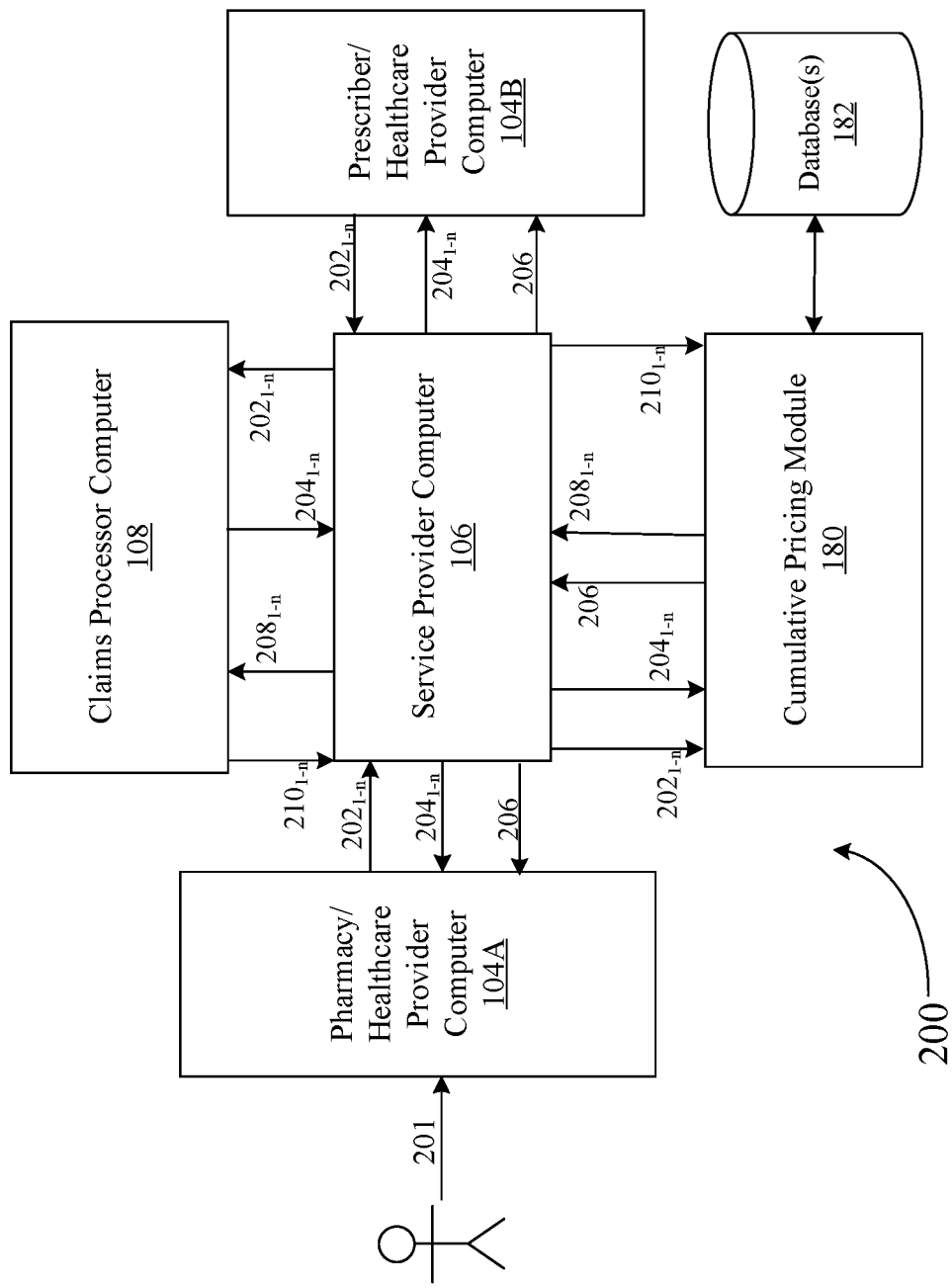
FIG. 2A is a diagram of an example data flow for determining patient financial responsibility for multiple prescription products as part of the processing of the healthcare transaction, according to one exemplary embodiment of the disclosure.
Figure 3:
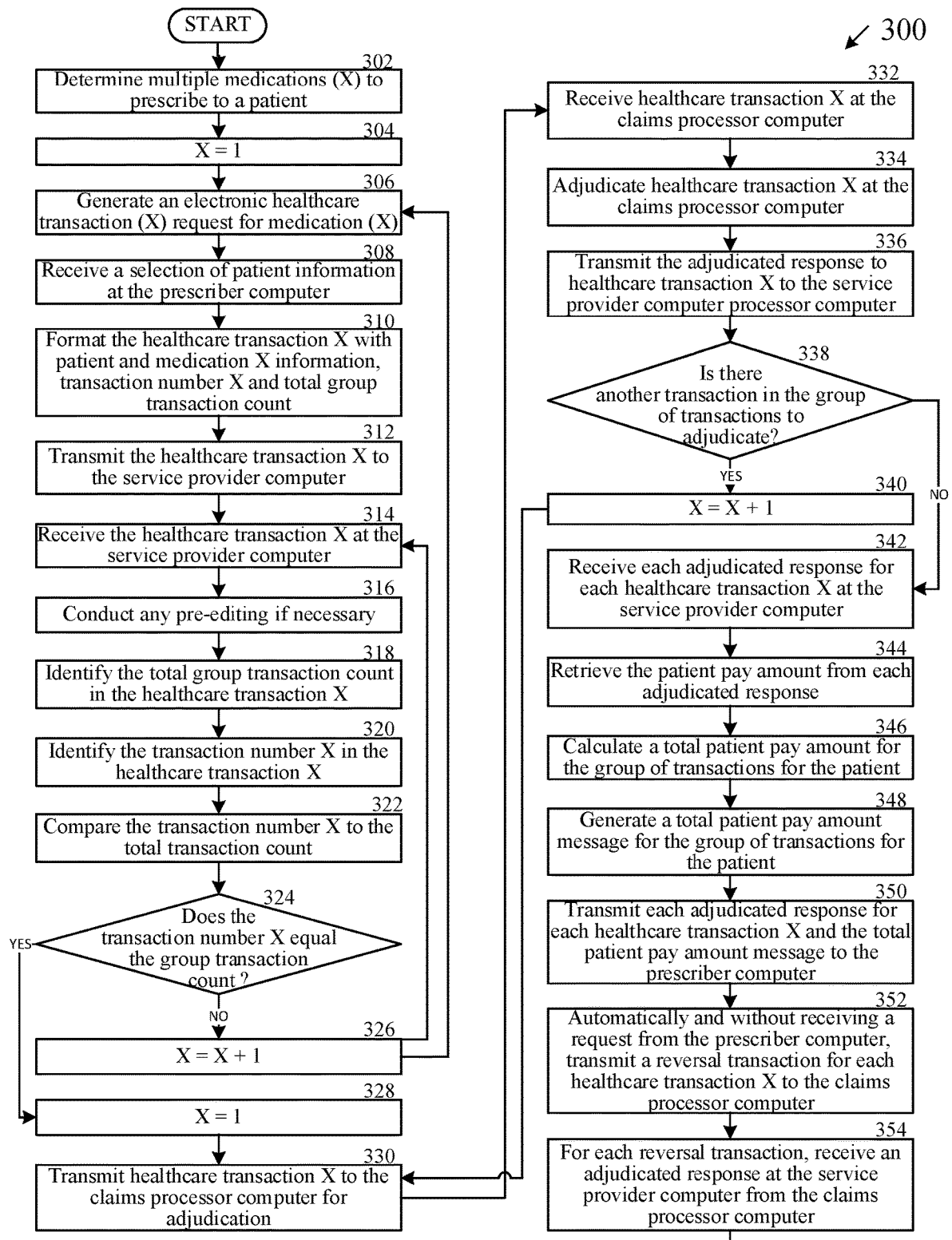
FIG. 3 is a flow chart of an example method for determining patient financial responsibility for multiple prescription products as part of the processing of the healthcare transaction, according to one exemplary embodiment of the disclosure.

FIG. 2A is a diagram of one example data flow 200 for determining patient financial responsibility for multiple prescription products as part of the processing of one or a group of healthcare transactions through a service provider computer, such as through the service provider computer 106 illustrated in FIG. 1. FIG. 3 is a flow chart of an example method 300 for determining patient financial responsibility for multiple prescription products, as part of the processing of one or multiple healthcare transactions (e.g., a predetermination of benefits transaction, a healthcare claim transaction, prescription claim or billing request, healthcare order transaction, or e-prescription transaction (e.g., electronic prescription order transaction, e-script, or e-prescription)) for that patient through a service provider computer 106, in accordance with one exemplary embodiment. All or a portion of the steps in the exemplary method 300, described below, may be performed by a suitable service provider computer 106 and/or cumulative pricing module 180.

The exemplary method 300 will be described with reference to a prescriber (e.g., physician, nurse, nurse practitioner, hospital or any other person legally permitted to prescribe medications to patients) as one healthcare provider (and accordingly a prescriber computer as the first healthcare provider computer 104B and a pharmacy as another healthcare provider (and accordingly a pharmacy computer as another healthcare provider computer 104A). However, this is only for purposes of example as other healthcare providers could be substituted for, and should each be individually read as being a part of this method. As such, where the discussion of the methods below and the drawings state a prescriber and/or a pharmacy, any other healthcare provider could be substituted, such as a physician, hospital, physician's office, clinic, or healthcare center.

In addition, the exemplary method 300 will be described with reference to a healthcare claim transaction; however, this also is only for purposes of example as other healthcare transactions, which may include, for example, a predetermination of benefits transaction, the healthcare claim transaction, prescription claim or billing request, healthcare order transaction, or e-prescription transaction (e.g., electronic prescription order transaction, e-script, or e-prescription) could be substituted for the healthcare claim transaction and each form of healthcare transaction should each individually be read as being used in the method described below.

Referring now to FIGS. 1, 2A, and 3, the exemplary method 300 begins at the START block and proceeds to block 302, where multiple products (e.g., medications) to prescribe to a patient are determined. In one example embodiment, the determination may be made by a prescriber of medications and products (e.g., physician, nurse, nurse practitioner, physician's assistant, hospital, or any other person legally permitted to prescribe medications to patients). At block 304, counter variable X can be set equal to one. For example, counter variable X may represent the number of healthcare claim transactions in the group of healthcare claim transactions that may be submitted to cover the multiple prescribed products/medications for the patient.

At block 306, a first electronic healthcare claim transaction $202_1$ is generated for the first healthcare claim transaction for the first medication or product to be prescribed to the patient. In one example embodiment, the first healthcare claim transaction $202_1$ may be generated by the prescriber computer 104B. A selection of patient information is received at the prescriber computer 104B at block 308. For example, the prescriber determines the patient's name and accesses the prescriber computer 104B, which receives a selection of patient information from the pharmacist via the I/O interface 128B. In one example, the prescriber accesses the prescriber computer 104B and accesses a database of patient information, which may be stored in memory 126B or in another database either local or remote from the prescriber computer 104B. The pharmacist can then select the name or other patient identification information in the patient information database that matches the name or other identification information of the patient.

At block 310, the healthcare claim transaction $202_1$ is formatted at the prescriber computer with the patient and medication/product information. In addition, the healthcare claim transaction $202_1$ may have fields that include data that represent a transaction number (e.g., 1 for the first healthcare claim transaction $202_1$) and a total group transaction count. In one example embodiment, the total group transaction count represents the total number of healthcare claim transactions $202_1$ that will be submitted for the patient by the prescriber. For example, if four products/medications are to be prescribed to the patient, four separate healthcare claim transactions may be submitted by the prescriber and the total group transaction count would be four.

In certain exemplary embodiments, the prescriber computer 104B formats the first healthcare claim transaction $202_1$ with patient information (e.g., patient identifiers), Payor ID/routing information (e.g., claims processor/destination identifiers), and medication/product information (e.g., medication/product identifiers). The information can be input into the first healthcare claim transaction $202_1$ by the prescriber via the I/O interface 128B or automatically retrieved and entered by the prescriber computer 104B and, in certain situations, can be based at least in part on historical transaction information for the patient in the data files 132B or a database communicably coupled to the prescriber computer 104B. According to one example embodiment, the healthcare claim transaction $202_1$ may be formatted in accordance with a version of the National Council for Prescription Drug Programs (NCPDP) Telecommunication Standard, although other standards, such as ANSI ASC X-12 Standard, Health Level 7 (HL7) Standard, or NCPDP Script Standard may be utilized as well.

The first healthcare claim transaction $202_1$ may include a Banking Identification Number (BIN Number), a BIN Number and Processor Control Number (PCN), or a BIN Number and Group ID for identifying a particular claims processor computer (e.g., ACO, PBM, payor, healthcare insurance company, Medicare or other government healthcare insurance payor, Medicare Part D provider, etc.), such as the claims processor computer 108, as a destination for the first healthcare claim transaction $202_1$. In addition, the first healthcare claim transaction $202_1$ may also include information relating to the patient, payor, prescriber, healthcare provider, and/or the requested product/medication. As an example, the first healthcare claim transaction $202_1$ may include one or more of the following information:

Payor ID/Routing Information (Destination Identifier)
BIN Number, BIN Number and PCN and/or BIN Number and Group ID, that designates a destination of a healthcare claim transaction $202_n$
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Total Group Transaction Count
Transaction Number
Date of Service.

The healthcare claim transaction $202_n$ can be used to determine if the claims processor associated with the claims processor computer 108 approves or rejects payment coverage for the product/medication being requested in the healthcare claim transaction $202_n$ and, if approved, the amount the claims processor will cover (or pay) for the product/medication being prescribed and how much the patient co-pay amount will be.

The prescriber computer 104B can transmit the first healthcare claim transaction $202_1$ to the service provider computer 106 at block 312. At block 314, the service provider computer 106 receives the first healthcare claim transaction $202_1$. For example, the first healthcare claim transaction $202_1$ can be transmitted by the prescriber computer 104B to the service provider computer 106 via the network 110. The service provider computer 106 may conduct any pre-editing, if necessary, on the first healthcare claim transaction $202_1$ at block 316. The pre-edits may include verifying, adding, and/or editing information included in the first healthcare claim transaction $202_1$ prior to it being communicated to a claims processor computer 108. For example, the service provider module 156 of the service provider computer 106 can parse the first healthcare claim transaction $202_1$ to determine/edit the financial fields, the service code, the quantity dispensed, and/or the patient age. Further, the service provider module 156 or another portion of the service provider computer 106 may determine if the first healthcare claim transaction $202_1$ includes an indicator (e.g., a total group transaction count in a predetermined field of the first healthcare claim transaction $202_1$) that multiple healthcare claim transactions $202_n$ are being submitted for the patient.

At block 318, the cumulative pricing module 180 or another portion of the service provider computer 106 may identify a total group transaction count in a previously agreed upon field of the first healthcare claim transaction $202_1$. In one example, the cumulative pricing module 180 or another portion of the service provider computer 106 may parse the received first healthcare claim transaction $202_1$ to identify a total group transaction count (e.g., an integer (generally greater than one) representing the number of healthcare claim transactions $202_n$ that are being submitted for the patient) in one or more fields of the first healthcare claim transaction $202_1$. For purposes of example discussions herein, the total group transaction count may be four.

In certain example embodiments, one or more other fields in the healthcare claim transactions $202_{1-n}$ may be identified, evaluated and compared to other healthcare claim transactions $202_n$ to determine if the each healthcare claim transaction is a member of the group of healthcare claim transactions for the identified patient. For example, the cumulative pricing module 180 or another portion of the service provider computer 106 may identify the BIN Number and Cardholder ID or BIN Number, Cardholder ID, and Person Code in predetermined fields of the first healthcare claim transaction $202_1$ as well as in the other healthcare claim transactions $202_n$ and can compare them, along with, optionally, one or more elements of the patient information provided above to determine if the BIN Number and Cardholder ID or BIN Number, Cardholder ID, and Person Code in each transaction match. The match can signify that the healthcare claim transactions with the matching data are part of a group of transactions along with or irrespective of a total group transaction count in the respective healthcare claim transactions. In other example embodiments, data in other fields (discussed above) of the healthcare claim transactions can be evaluated rather than or in addition to the preceding to determine if the data in the fields match and to improve the likelihood that the healthcare claim transactions having the matching fields are part of a group of transactions.

At block 320, the cumulative pricing module 180 or another portion of the service provider computer 106 may identify a transaction number for the current healthcare claim transaction $202_1$ in a previously agreed upon field of the first healthcare claim transaction $202_1$. In one example, the cumulative pricing module 180 or another portion of the service provider computer 106 may parse the received first healthcare claim transaction $202_1$ to identify the transaction number (e.g., an integer representing the number of the current healthcare claim transactions $202_n$ as part of the group of healthcare claim transactions that are being submitted for the patient) in one or more fields of the first healthcare claim transaction $202_1$. In an example where the total group transaction count is four, the transaction number may be one, two, three, or four, depending on transaction number in the particular healthcare claim transaction $202_n$. For example, for the first healthcare claim transaction $202_1$ being submitted as part of a group of healthcare claim transactions for the patient, the transaction number would equal one.

At block 322, the transaction number from the first healthcare claim transaction $202_1$ is compared to the total group transaction count. In one example embodiment, the comparison is made by the cumulative pricing module 180 or another portion of the service provider computer 106 to determine if the transaction number equals the total group transaction count. Alternatively, the transaction numbers for each group of healthcare claim transactions $202_n$ may be identified and stored in the database 182 and may be checked by the cumulative pricing module 180 or another portion of the service provider computer 106 to determine if all of the healthcare claim transactions $202_n$ have been received. This will cover the potential issue of healthcare claims transactions $202_n$ being received and evaluated in an order other than how they were originally generated and sent out from the prescriber computer.

In block 324, an inquiry is conducted to determine if the transaction number in the first healthcare claim transaction $202_1$ matches the total group transaction count. Alternatively, the inquiry can be whether all of the transactions in the group of transactions have been received based on the total group transaction count and the transaction numbers received and stored in, for example, the database 182. If the transaction number in the current healthcare claim transaction (such as the first healthcare claim transaction $202_1$) does not equal the total group transaction count, the NO branch is followed to block 326. Similarly, in the alternate embodiment, if the cumulative pricing module 180 or another portion of the service provider computer 106 determines that not all of the transaction numbers for the total group transaction count have been identified (e.g., total group transaction count is four, but that only transaction numbers one and two have been identified in reviewed transactions), the NO branch may also be followed to block 326. In block 326, the counter variable X is incremented by one and the process may return to block 306 or 314 for the generation and/or receipt of the next healthcare claim transaction $202_{n+1}$. On the other hand, if the transaction number does equal the total group transaction count or all of the transaction numbers for the total group transaction count have been identified, the YES branch can be followed to block 328, where the counter variable X is reset to 1.

In block 330, the first healthcare claim transaction $202_1$ can be transmitted to the claims processor computer 108. For example, the first healthcare claim transaction $202_1$ may be electronically transmitted by the service provider computer 106 to the claims processor computer identified in the transaction $202_1$ via the network 110. In block 332, the particular claims processor computer 108 may receive the first healthcare claim transaction $202_1$. At block 334, the claims processor computer 108 may adjudicate the first healthcare claim transaction $202_1$ to determine if the patient has coverage, to determine to what extent the patient's coverage covers the requested medication/product identified in the first healthcare claim transaction $202_1$ and to generate a first adjudicated response $204_1$ to the first healthcare claim transaction $202_1$ as to whether the transaction $202_1$ is approved or rejected. Example adjudications $204_1$ can include, but are not limited to, accepted, approved, paid, captured, denied, and denied with request for additional information and resubmission. In certain exemplary embodiments, the adjudication $204_n$ can be input into a field of the corresponding healthcare claim transaction 202—that is recognized by the service provider computer 106 and/or the prescriber computer 104B. Typically, if the healthcare claim transaction $202_n$ is approved, the adjudicated response $204_n$ provides the amount of the cost of the medication, product, or service that will be covered by the claims processor associated with the claims processor computer 108 and the patient co-pay amount and if rejected, the adjudicated response $204_n$ provides the reason for the rejection (e.g., patient not covered, Cardholder ID submitted in the transaction is inactive, prior authorization required, medication not covered, etc.), such as in the form of a reject code.

At block 336, the claims processor computer 108 can transmit the adjudicated response $204_1$ to the first healthcare claim transaction $202_1$ to the cumulative pricing module and/or the service provider computer 106 via the network 110. At block 338, an inquiry may be conducted to determine if there is another healthcare claim transaction $202_n$ in the group of healthcare claim transactions to be adjudicated by the claims processor computer 108. In one example embodiment, the determination can be made by the cumulative pricing module 180 or another portion of the service provider computer 106 in a manner substantially similar to that described in blocks 322 and 324 above except that the transaction numbers for the adjudicated responses $204_n$ may be compared or otherwise evaluated against the total group transaction count for the group of transactions. If another transaction $202_n$ in the group of healthcare transactions needs to be adjudicated, then the YES branch may be followed to block 340, where the counter variable X is incremented by one and the process returns to block 330 where the next healthcare claim transaction $202_n$ may be transmitted to the claims processor computer for adjudication. Alternatively, all of the transactions $202_n$ may have previously been sent and the cumulative pricing module 180 or another portion of the service provider computer may be awaiting receipt of all of the adjudicated responses $204_n$. If there are no addition healthcare claim transactions $202_n$ in the group of healthcare claim transactions for the patient that still need to be adjudicated and received back at the cumulative pricing module 180 or service provider computer 106, then the NO branch may be followed to block 342.

At block 342, the cumulative pricing module 180 or another portion of the service provider computer 106 may receive each adjudicated response $204_n$ for each of the healthcare claim transactions $202_n$ in the group of healthcare claim transactions for the patient. For example the service provider computer 106 may receive each adjudicated response $204_n$ and may transmit that adjudicated response $204_n$ to the cumulative pricing module 180 for further evaluation.

At block 344, the cumulative pricing module 180 or another portion of the service provider computer 106 may retrieve or otherwise identify the patient co-pay amount from each adjudicated response $204_{1-n}$. In one example, the cumulative pricing module 180 or another portion of the service provider computer 106 may parse each of the received adjudicated responses $204_{1-n}$ to identify a patient co-pay amount (e.g., the amount the patient is responsible for paying for the prescribed product/medication) in a predetermined field of each adjudicated response $204_{1-n}$. As discussed above, the patient co-pay amount may be the same or different in each adjudicated response $204_{1-n}$ based on different co-pay levels for different types of products, whether deductibles have been met, whether deductibles may affect the co-pay amounts, and whether certain products/medications are or are not covered and the level of coverage (either flat co-pay or percentage of total cost) for each. In certain example embodiments, as the cumulative pricing module 180 or another portion of the service provider computer 106 identifies the patient co-pay amount in each adjudicated response $204_n$, the patient co-pay amount may be stored in the database 182 and/or data files 148 for further evaluation.

At block 346, the cumulative pricing module 180 or another portion of the service provider computer 106 can calculate a total patient pay amount for the group of healthcare claim transactions $202_n$. For example, the cumulative pricing module 180 may collect each of the identified patient co-pay amounts and can calculate the sum total of the identified patient co-pay amounts for the group of healthcare claim transactions $202_n$. For example, if the individual co-pay amounts for the group of four healthcare claim transactions $202_n$ for the patient were $25, $50, $10, and $35, the cumulative pricing module 180 could calculate the sum as the total patient pay amount of $120. In certain example embodiments, some of the group of healthcare claim transactions $202_n$ may have been approved during adjudication and provided a patient co-pay amount while others may be have been denied or otherwise rejected/returned without approval. In these examples, the total patient pay amount may be calculated only for those healthcare claim transactions $202_n$ that were approved. At block 348, the cumulative pricing module 180 or another portion of the service provider computer 106 can generate a total patient pay amount message 206 for the group of healthcare claim transactions $202_n$ for the patient. In certain example embodiments, the total patient pay amount message may include the number of transactions and the calculated total patient pay amount and may be inserted into a text or other predetermined field of one or more of the adjudicated responses $204_{1-n}$ or may be a separate message sent with one or more of the adjudicated responses $204_{1-n}$ to the prescriber computer 104B.

At block 350, the service provider computer 106 may transmit each adjudicated response $204_{1-n}$ for each healthcare claim transaction $202_n$ in the group of transactions and the total patient pay amount message to the prescriber computer 104B via, for example, the network 110. At block 352, automatically and without receiving a request from the prescriber computer 104B or any other remote computer, the cumulative pricing module 180 or another portion of the service provider computer 106 can generate a reversal transaction $208_{1-n}$ corresponding to each of the healthcare claim transactions $202_{1-n}$ in the group of transactions to cancel out each of the healthcare claim transactions $202_{1-n}$, and may transmit each of the reversal transactions $208_{1-n}$ from the cumulative pricing module 180 or the service provider computer 106 to the corresponding claims processor computer(s) 108 that received each of the healthcare claim transactions $202_{1-n}$ via, for example, the network 110. In certain example embodiments, some of the healthcare claim transactions $202_{1-n}$ may have been approved during adjudication while other ones of the healthcare claim transactions $202_{1-n}$ may be have been denied or otherwise rejected/returned without approval. In these examples, the reversal transactions $208_{1-n}$ may only be generated and transmitted for only those healthcare claim transactions $202_{1-n}$ that were approved. At block 354, after adjudication of each of the reversal transactions $208_{1-n}$ by the claims processor computer 108, the cumulative pricing module 180 or another portion of the service provider computer 106 may receive the adjudicated responses $210_{1-n}$ for each of the reversal transactions $208_{1-n}$. The process may continue to the END block.

Figure 4:
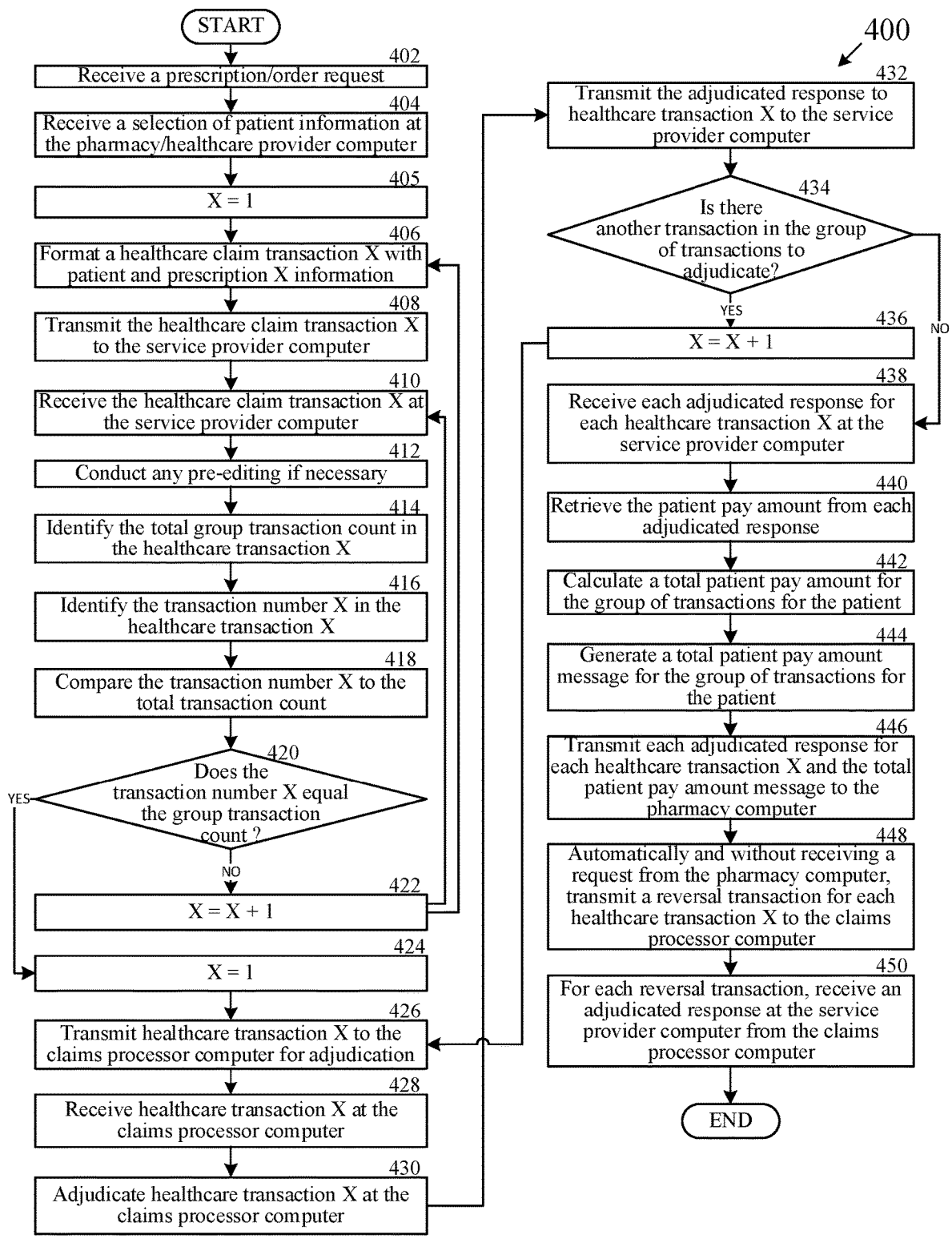
FIG. 4 is a flow chart of another example method for determining patient financial responsibility for multiple prescription products as part of the processing of the healthcare transaction, according to an alternative exemplary embodiment of the disclosure.

FIG. 4 is a flow chart of another example method 400 for determining patient financial responsibility for multiple prescription products, as part of the processing of one or multiple healthcare transactions (e.g., a predetermination of benefits transaction, a healthcare claim transaction, prescription claim or billing request, healthcare order transaction, or e-prescription transaction (e.g., electronic prescription order transaction, e-script, or e-prescription)) for that patient through a service provider computer 106, in accordance with an alternative exemplary embodiment. All or a portion of the steps in the exemplary method 400, described below, may be performed by a suitable service provider computer 106 and/or cumulative pricing module 180.

The exemplary method 400 will be described with reference to a pharmacy/pharmacist as the healthcare provider (and accordingly a pharmacy computer 104A as the first healthcare provider computer 104A. However, this is only for purposes of example as other healthcare providers could be substituted for, and should each be individually read as being a part of this method. As such, where the discussion of the methods below and the drawings state a pharmacy or pharmacist, any other healthcare provider could be substituted, such as a physician, hospital, physician's office, clinic, or healthcare center.

In addition, the exemplary method 400 will be described with reference to a healthcare claim transaction; however, this also is only for purposes of example as other healthcare transactions, which may include, for example, a predetermination of benefits transaction, the healthcare claim transaction, prescription claim or billing request, healthcare order transaction, or e-prescription transaction (e.g., electronic prescription order transaction, e-script, or e-prescription) could be substituted for the healthcare claim transaction and each form of healthcare transaction should each individually be read as being used in the method described below.

Referring now to FIGS. 1, 2A, and 4, the exemplary method 400 begins at the START block and proceeds to block 402, where one or more prescription/order requests 201 are received. In one example embodiment, the prescription/order request 201 is multiple prescription/order requests, each identifying a prescribed medication/product for the patient. Alternatively, the prescription/order request 201 includes multiple products/medications prescribed for the patient. In one example, embodiment, the prescription/order request 201 is received by a pharmacist at a pharmacy. For example, the prescription/order request 201 may be received from a patient, another healthcare provider prescribing a medication or service (e.g., physician, clinic, physician's office, hospital, etc.), by phone, via the Internet, via an e-prescription transaction or by way of an electronic system order. For example, the prescription 201 may be received by the patient from a prescriber of the medication, such as a doctor, dentist, nurse, physician's assistant, or any other person legally authorized to prescribe medications, products, and/or services for a patient. The patient may go to the location of the pharmacy and physically hand the prescription request 201 to the pharmacist or make a request via a web portal communicably coupled to the pharmacy computer 104A or an IVR communicably coupled or otherwise providing order data to the pharmacy computer 104A. The pharmacist determines the patient's name and accesses the pharmacy computer 104A, which receives a selection of patient information from the pharmacist via the I/O interface 164 at block 404. For example, the pharmacist accesses the pharmacy computer 104A and accesses a database of patient information, which may be stored in memory 126A or in another database either local or remote from the pharmacy computer 104A. The pharmacist can then select the name or other patient identification information in the patient information database that matches the name or other identification information of the patient.

At block 405, counter variable X can be set equal to one. For example, counter variable X may represent the number of healthcare claim transactions in the group of healthcare claim transactions that may be submitted to cover the multiple prescribed products/medications for the patient. At block 406, a first electronic healthcare claim transaction $202_1$ is generated and/or formatted for the first medication or product prescribed to the patient. In one example embodiment, the first healthcare claim transaction $202_1$ may be generated by the pharmacy computer 104A. In certain exemplary embodiments, the pharmacy computer 104A formats the healthcare claim transaction $202_1$ with patient information (e.g., patient identifiers), Payor ID/routing information (e.g., claims processor/destination identifiers), and product/medication information (e.g., medication/product identifiers). In addition, the healthcare claim transaction $202_1$ may have fields that include data that represent a transaction number (e.g., 1 for the first healthcare claim transaction $202_1$, 2 for a second healthcare claim transaction $202_2$ and so on) and a total group transaction count. In one example embodiment, the total group transaction count represents the total number of healthcare claim transactions $202_n$ that will be submitted for the patient by the pharmacist or other pharmacy employee via the pharmacy computer 104A to the service provider computer 106. For example, if four products/medications are prescribed to the patient, four separate healthcare claim transactions $202_{1-4}$ may be submitted by the pharmacy via the pharmacy computer 104A and the total group transaction count would be four. The information can be input into the healthcare claim transaction $202_1$ by the pharmacist via the I/O interface 128A or automatically retrieved and entered by the pharmacy computer 104A and, in certain situations, can be based at least in part on historical transaction information for the patient in the data files 132A or a database communicably coupled to the pharmacy computer 104A. According to one example embodiment, the first healthcare claim transaction $202_1$ may be formatted in accordance with a version of the National Council for Prescription Drug Programs (NCPDP) Telecommunication Standard, although other standards, such as ANSI ASC X-12 Standard, Health Level 7 (HL7) Standard, or NCPDP Script Standard may be utilized as well.

The first healthcare claim transaction $202_1$ may include a Banking Identification Number (BIN Number), a BIN Number and Processor Control Number (PCN), or a BIN Number and Group ID for identifying a particular claims processor computer (e.g., ACO, PBM, payor, healthcare insurance company, Medicare or other government healthcare insurance payor, Medicare Part D provider, etc.), such as the claims processor computer 108, as a destination for the first healthcare claim transaction $202_1$. In addition, the first healthcare claim transaction $202_1$ may also include information relating to the patient, payor, prescriber, healthcare provider, and/or the requested product/medication. As an example, the first healthcare claim transaction $202_1$ may include one or more of the following information:

Payor ID/Routing Information (Destination Identifier)
BIN Number, BIN Number and PCN and/or BIN Number and Group ID, that designates a destination of a healthcare claim transaction $202_n$
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)

Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Total Group Transaction Count
Transaction Number
Date of Service.

The healthcare claim transaction $202_n$ can be used to determine if the claims processor associated with the claims processor computer 108 approves or rejects payment coverage for the product/medication being requested in the healthcare claim transaction $202_n$ and, if approved, the amount the claims processor will cover (or pay) for the product/medication being prescribed and how much the patient co-pay amount will be.

The pharmacy computer 104A can transmit the first healthcare claim transaction $202_1$ to the service provider computer 106 at block 408. At block 410, the service provider computer 106 receives the first healthcare claim transaction $202_1$. For example, the first healthcare claim transaction $202_1$ can be transmitted by the pharmacy computer 104A to the service provider computer 106 via the network 110. The service provider computer 106 may conduct any pre-editing, if necessary, on the first healthcare claim transaction $202_1$ at block 412. The pre-edits may include verifying, adding, and/or editing information included in the first healthcare claim transaction $202_1$ prior to it being communicated to a claims processor computer 108. For example, the service provider module 156 of the service provider computer 106 can parse the first healthcare claim transaction $202_1$ to determine/edit the financial fields, the service code, the quantity dispensed, and/or the patient age. Further, the service provider module 156 or another portion of the service provider computer 106 may determine if the first healthcare claim transaction $202_1$ includes an indicator (e.g., a total group transaction count in a predetermined field of the first healthcare claim transaction $202_1$) that multiple healthcare claim transactions $202_n$ are being submitted for the patient.

At block 414, the cumulative pricing module 180 or another portion of the service provider computer 106 may identify a total group transaction count in a previously agreed upon field of the first healthcare claim transaction $202_1$. In one example, the cumulative pricing module 180 or another portion of the service provider computer 106 may parse the received first healthcare claim transaction $202_1$ to identify a total group transaction count (e.g., an integer (generally greater than one) representing the number of healthcare claim transactions $202_n$ that are being submitted for the patient) in one or more fields of the first healthcare claim transaction $202_1$. For purposes of example discussions herein, the total group transaction count may be four.

In certain example embodiments, one or more other fields in the healthcare claim transactions $202_{1-n}$ may be identified, evaluated and compared to other healthcare claim transactions $202_n$ to determine if the each healthcare claim transaction is a member of the group of healthcare claim transactions for the identified patient. For example, the cumulative pricing module 180 or another portion of the service provider computer 106 may identify the BIN Number and Cardholder ID or BIN Number, Cardholder ID, and Person Code in predetermined fields of the first healthcare claim transaction $202_1$ as well as in the other healthcare claim transactions $202_n$ and can compare them, along with, optionally, one or more elements of the patient information provided above to determine if the BIN Number and Cardholder ID or BIN Number, Cardholder ID, and Person Code in each transaction match. The match can signify that the healthcare claim transactions with the matching data are part of a group of transactions along with or irrespective of a total group transaction count in the respective healthcare claim transactions. In other example embodiments, data in other fields (discussed above) of the healthcare claim transactions can be evaluated rather than or in addition to the preceding to determine if the data in the fields match and to improve the likelihood that the healthcare claim transactions having the matching fields are part of a group of transactions.

At block 416, the cumulative pricing module 180 or another portion of the service provider computer 106 may identify a transaction number for the current healthcare claim transaction $202_1$ in a previously agreed upon field of the first healthcare claim transaction $202_1$. In one example, the cumulative pricing module 180 or another portion of the service provider computer 106 may parse the received first healthcare claim transaction $202_1$ to identify the transaction number (e.g., an integer representing the number of the current healthcare claim transactions $202_n$ as part of the group of healthcare claim transactions that are being submitted for the patient) in one or more fields of the first healthcare claim transaction $202_1$. In an example where the total group transaction count is four, the transaction number may be one, two, three, or four, depending on transaction number in the particular healthcare claim transaction $202_n$. For example, for the first healthcare claim transaction $202_1$ being submitted as part of a group of healthcare claim transactions for the patient, the transaction number would equal one.

At block 418, the transaction number from the first healthcare claim transaction $202_1$ is compared to the total group transaction count identified in the healthcare claim transaction $202_n$. In one example embodiment, the comparison is made by the cumulative pricing module 180 or another portion of the service provider computer 106 to determine if the transaction number equals the total group transaction count. Alternatively, the transaction numbers for each group of healthcare claim transactions $202_n$ may be identified and stored in the database 182 and may be checked by the cumulative pricing module 180 or another portion of the service provider computer 106 to determine if all of the healthcare claim transactions $202_n$ have been received. This will cover the potential issue of healthcare claims transactions $202_n$ being received and evaluated in an order other than how they were originally generated and sent out from the pharmacy computer 104A.

At block 420, an inquiry is conducted to determine if the transaction number in the first healthcare claim transaction $202_1$ matches the total group transaction count. Alternatively, the inquiry can be whether all of the transactions in the group of transactions have been received based on the total group transaction count and the transaction numbers received and stored in, for example, the database 182. If the transaction number in the current healthcare claim transaction (such as the first healthcare claim transaction $202_1$) does not equal the total group transaction count, the NO branch is followed to block 422. Similarly, in the alternate embodiment, if the cumulative pricing module 180 or another portion of the service provider computer 106 determines that not all of the transaction numbers for the total group transaction count have been identified (e.g., total group transaction count is four, but that only transaction numbers one and two have been identified in reviewed transactions), the NO branch may also be followed to block 422. At block 422, the counter variable X is incremented by one and the process may return to block 406 or 410 for the generation and/or receipt of the next healthcare claim transaction $202_{n+1}$. On the other hand, if the transaction number does equal the total group transaction count or all of the transaction numbers for the total group transaction count have been identified, the YES branch can be followed to block 424, where the counter variable X is reset to 1.

In block 424, the first healthcare claim transaction $202_1$ can be transmitted to the claims processor computer 108 for adjudication. For example, the first healthcare claim transaction $202_1$ may be electronically transmitted by the service provider computer 106 to the claims processor computer 108 identified (e.g., via BIN Number, BIN Number and PCN, or BIN Number and Group ID) in the transaction $202_1$ via the network 110. At block 428, the particular claims processor computer 108 may receive the first healthcare claim transaction $202_1$. At block 430, the claims processor computer 108 may adjudicate the first healthcare claim transaction $202_1$ to determine if the patient has coverage, to determine to what extent the patient's coverage covers the requested medication/product identified in the first healthcare claim transaction $202_1$ and to generate a first adjudicated response $204_1$ to the first healthcare claim transaction $202_1$ as to whether the transaction $202_1$ is approved or rejected. Example adjudications $204_1$ can include, but are not limited to, accepted, approved, paid, captured, denied, and denied with request for additional information and resubmission. In certain exemplary embodiments, the adjudication $204_n$ can be input into a field of the corresponding healthcare claim transaction 202—that is recognized by the service provider computer 106 and/or the pharmacy computer 104A. Typically, if the healthcare claim transaction $202_n$ is approved, the adjudicated response $204_n$ provides the amount of the cost of the medication, product, or service that will be covered by the claims processor associated with the claims processor computer 108 and the patient co-pay amount and if rejected, the adjudicated response $204_n$ provides the reason for the rejection (e.g., patient not covered, Cardholder ID submitted in the transaction is inactive, prior authorization required, medication not covered, etc.), such as in the form of a reject code.

At block 432, the claims processor computer 108 can transmit the adjudicated response $204_1$ to the first healthcare claim transaction $202_1$ to the cumulative pricing module and/or the service provider computer 106 via the network 110. At block 434, an inquiry may be conducted to determine if there is another healthcare claim transaction $202_n$ in the group of healthcare claim transactions to be adjudicated by the claims processor computer 108. In one example embodiment, the determination can be made by the cumulative pricing module 180 or another portion of the service provider computer 106 in a manner substantially similar to that described in blocks 418 and 420 above except that the transaction numbers for the adjudicated responses $204_n$ may be compared or otherwise evaluated against the total group transaction count for the group of transactions. If another transaction $202_n$ in the group of healthcare transactions needs to be adjudicated, then the YES branch may be followed to block 436, where the counter variable X is incremented by one and the process returns to block 426 where the next healthcare claim transaction $202_n$ may be transmitted to the claims processor computer 108 for adjudication. Alternatively, all of the transactions $202_n$ may have previously been sent and the cumulative pricing module 180 or another portion of the service provider computer 106 may be awaiting receipt of all of the adjudicated responses $204_n$. If there are no addition healthcare claim transactions $202_n$ in the group of healthcare claim transactions for the patient that still need to be adjudicated and received back at the cumulative pricing module 180 or service provider computer 106, then the NO branch may be followed to block 438.

At block 438, the cumulative pricing module 180 or another portion of the service provider computer 106 may receive each adjudicated response $204_n$ for each of the healthcare claim transactions $202_n$ in the group of healthcare claim transactions for the patient. For example the service provider computer 106 may receive each adjudicated response $204_n$ and may transmit that adjudicated response $204_n$ to the cumulative pricing module 180 for further evaluation.

At block 440, the cumulative pricing module 180 or another portion of the service provider computer 106 may retrieve or otherwise identify the patient co-pay amount from each adjudicated response $204_{1-n}$. In one example, the cumulative pricing module 180 or another portion of the service provider computer 106 may parse each of the received adjudicated responses $204_{1-n}$ to identify a patient co-pay amount (e.g., the amount the patient is responsible for paying for the prescribed product/medication) in a predetermined field of each adjudicated response $204_{1-n}$. As discussed above, the patient co-pay amount may be the same or different in each adjudicated response $204_{1-n}$ based on different co-pay levels for different types of products, whether deductibles have been met, whether deductibles may affect the co-pay amounts, and whether certain products/medications are or are not covered and the level of coverage (either flat co-pay or percentage of total cost) for each. In certain example embodiments, as the cumulative pricing module 180 or another portion of the service provider computer 106 identifies the patient co-pay amount in each adjudicated response $204_n$, the patient co-pay amount may be stored in the database 182 and/or data files 148 for further evaluation.

At block 442, the cumulative pricing module 180 or another portion of the service provider computer 106 can calculate a total patient pay amount for the group of healthcare claim transactions $202_n$. For example, the cumulative pricing module 180 may collect each of the identified patient co-pay amounts and can calculate the sum total of the identified patient co-pay amounts for the group of healthcare claim transactions $202_n$. For example, if the individual co-pay amounts for the group of four healthcare claim transactions $202_n$ for the patient were $25, $50, $10, and $35, the cumulative pricing module 180 could calculate the sum as the total patient pay amount of $120. In certain example embodiments, some of the group of healthcare claim transactions 202$_n$ may have been approved during adjudication and provided a patient co-pay amount while others may be have been denied or otherwise rejected/returned without approval. In these examples, the total patient pay amount may be calculated only for those healthcare claim transactions 202$_n$ that were approved. At block 444, the cumulative pricing module 180 or another portion of the service provider computer 106 can generate a total patient pay amount message 206 for the group of healthcare claim transactions 202$_n$ for the patient. In certain example embodiments, the total patient pay amount message may include the number of transactions and the calculated total patient pay amount and may be inserted into a text or other predetermined field of one or more of the adjudicated responses 204$_{1-n}$ or may be a separate message sent with one or more of the adjudicated responses 204$_{1-n}$ to the pharmacy computer 104A.

At block 446, the service provider computer 106 may transmit each adjudicated response 204$_{1-n}$ for each healthcare claim transaction 202$_n$ in the group of transactions and the total patient pay amount message to the pharmacy computer 104A via, for example, the network 110. At block 448, automatically and without receiving a request from the pharmacy computer 104A or any other remote computer, the cumulative pricing module 180 or another portion of the service provider computer 106 can generate a reversal transaction 208$_{1-n}$ corresponding to each of the healthcare claim transactions 202$_{1-n}$ in the group of transactions to cancel out each of the healthcare claim transactions 202$_{1-n}$, and may transmit each of the reversal transactions 208$_{1-n}$ from the cumulative pricing module 180 or the service provider computer 106 to the corresponding claims processor computer(s) 108 that received each of the healthcare claim transactions 202$_{1-n}$ via, for example, the network 110. In certain example embodiments, some of the healthcare claim transactions 202$_{1-n}$ may have been approved during adjudication while other ones of the healthcare claim transactions 202$_{1-n}$ may have been denied or otherwise rejected/returned without approval. In these examples, the reversal transactions 208$_{1-n}$ may only be generated and transmitted for only those healthcare claim transactions 202$_{1-n}$ that were approved. At block 450, after adjudication of each of the reversal transactions 208$_{1-n}$ by the claims processor computer 108, the cumulative pricing module 180 or another portion of the service provider computer 106 may receive the adjudicated responses 210$_{1-n}$ for each of the reversal transactions 208$_{1-n}$. The process may continue to the END block.

The methods described and shown in FIGS. 3 and 4 may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3 and 4 may be performed.

Figure 2B:
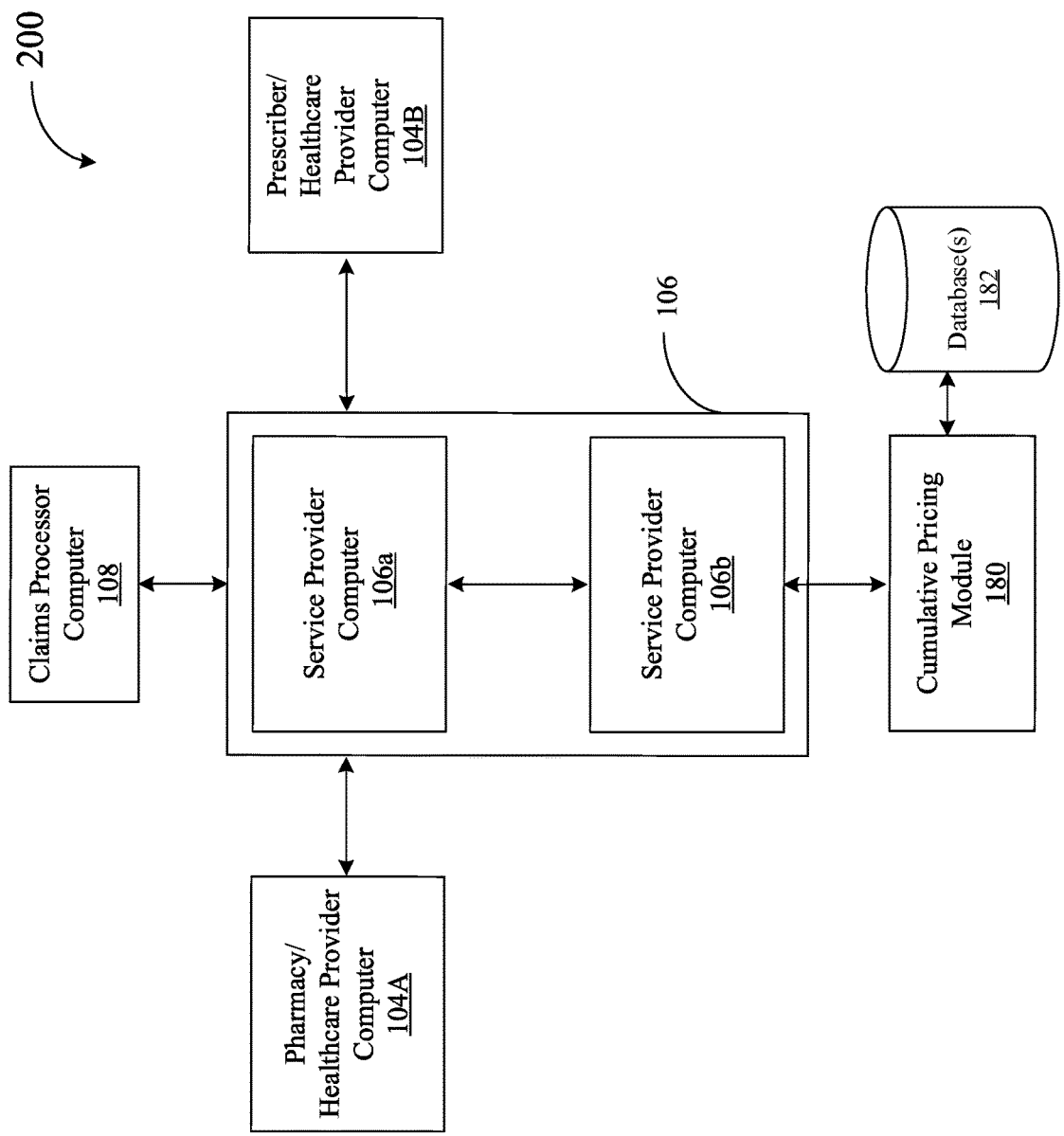
FIG. 2B is a diagram of another example data flow for determining patient financial responsibility for multiple prescription products as part of the processing of the healthcare transaction processed through one or more service providers, according to an alternative exemplary embodiment of the disclosure.

Likewise, while FIGS. 3 and 4 have been described primarily in conjunction with FIG. 2A, it will be appreciated that variations of FIG. 2A are available. As shown by FIG. 2B, the service provider computer 106 may include two or more distinct service provider computers 106a and 106b that are in communication with each other. These distinct service provider computers 106a and 106b may be owned, operated, and/or located by the same or distinct and wholly-unrelated companies. The service provider computer 106a may be operative with the pharmacy computer 104A and the prescriber computer 104B, while the service provider computer 106b may be operative with other healthcare provider computers and/or other third-party entity computers. However, the service provider computer 106b may have a data processing arrangement with the service provider computer 106a. Under the data processing arrangement, the service provider computer 106a may be permitted to utilize or offer services of the service provider computer 106b, including the operations and use of the cumulative pricing module 180 and/or the database 182 to conduct cumulative pricing determinations of patient financial responsibility for multiple prescription products/medications by evaluating healthcare transactions, as discussed above in FIGS. 3 and 4. Accordingly, the services accessible by the service provider computer 106b, including the cumulative pricing assessments for multiple prescription products/medications for patients, may be available to the pharmacy computer 104A and/or the prescriber computer 104B via the service provider computers 106a and 106b.

Accordingly, example embodiments disclosed herein can provide the technical effects of creating a system and methods that provide a real-time or near real time way to evaluate healthcare transactions to determine patient financial responsibility amounts for multiple prescription products/medications. In this regard, pharmacists and prescribers of medications will be able to provide more accurate pricing information to patients with regard to their prescriptions and may be able to determine if the patient will agree to pay the determined amount. This can lead to a better determination as to whether the patient will adhere to the prescription protocol which will likely lead to better health for the patient.

While certain example embodiments disclosed herein describe the cumulative pricing module 180 as being separate of the service provider computer 106, in alternate embodiments, the cumulative pricing module 180 or the functions that it completes may be part of the service provider computer 106. In those embodiments where the cumulative pricing module 180 is incorporated into the service provider computer 106, and with regard to the methods described above, the elements describing transmitting or receiving between the service provider computer 106 and the cumulative pricing module 180 may be internal transmissions within the service provider computer 106 or may be omitted altogether. Further, while the exemplary embodiments described herein disclose certain steps occurring at the service provider computer 106 and/or the cumulative pricing module 180, in alternative embodiments those steps described with reference to FIGS. 1-4 may alternately be completed at a pharmacy computer 104A, a prescriber computer 104B, or another healthcare provider computer 104 (e.g., a hospital computer, clinic computer, etc.) a claims processor computer 108, a cumulative pricing module 180, any combination thereof, and/or a combination of those devices along with the service provider computer 106. In those alternate embodiments, certain transmission/receiving blocks described above with reference to FIGS. 1-4 may be omitted while others may be added, as understood by one or ordinary skill in the art. The intent being that, in alternate embodiments, any of the devices/computers discussed in FIG. 1 are capable of completing all or any part of the methods described with reference to FIGS. 2A-4.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, that includes a computer usable medium (e.g., transitory or non-transitory) having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method, comprising:
   receiving, by a service provider computer associated with a service provider and comprising one or more processors from a healthcare provider computer associated with a healthcare provider, a first healthcare transaction comprising a first medication identifier identifying a first medication to be prescribed to a patient, a first total group transaction number identifying a total number of healthcare transactions included in a first group, the total number of healthcare transactions being greater than one; a first transaction number identifier; and a first patient identifier identifying the patient to receive the first medication;
   identifying, by the service provider computer, the first total group transaction number and the first transaction number identifier in the first healthcare transaction;
   comparing, by the service provider computer, the first transaction number identifier to the first total group transaction number to determine if the first transaction number identifier equals the first total group transaction number;
   in accordance with a determination that the first transaction number identifier equals the first total group transaction number, transmitting, by the service provider computer, the first healthcare transaction to a claims processor computer of a claims processor for adjudication;
   receiving, by the service provider computer, a first adjudicated response to the first healthcare transaction;
   identifying, by the service provider computer, a first patient co-pay amount in the first adjudicated response;
   transmitting, by the service provider computer, a total patient pay amount at least partially based upon the first patient co-pay amount to the healthcare provider computer;
   generating, by the service provider computer automatically and without receiving a reversal request from the healthcare provider computer, a first reversal transaction for the first healthcare transaction;
   transmitting, by the service provider computer, the first reversal transaction to the claims processor computer; and
   receiving, by the service provider computer from the claims processor computer, a first adjudicated response to the first reversal transaction.

2. The computer-implemented method of claim 1, further comprising:
   receiving, by the service provider computer from the healthcare provider computer, a second healthcare transaction comprising a second medication identifier identifying a second medication to be prescribed to the patient, the first total group transaction number; a second transaction number identifier, and the first patient identifier;
   transmitting, by the service provider computer, the second healthcare transaction to the claims processor computer of the claims processor for adjudication;
   receiving, by the service provider computer, a second adjudicated response to the second healthcare transaction; and
   identifying, by the service provider computer, a second patient co-pay amount in the second adjudicated response; and calculating, by the service provider computer, the total patient pay amount based on the first patient co-pay amount and the second patient co-pay amount.

3. The computer-implemented method of claim 2, wherein the total patient pay amount is the sum of the first patient co-pay amount and the second patient co-pay amount.

4. The computer-implemented method of claim 1, further comprising:
   generating, by the service provider computer, a total patient pay amount message comprising the total patient pay amount; and inserting, by the service provider computer, the total patient pay amount message into the first adjudicated response.

5. The computer-implemented method of claim 1, wherein the healthcare provider computer is a pharmacy computer and the healthcare provider is a pharmacy.

6. The computer-implemented method of claim 1, wherein the healthcare provider computer is a prescriber computer and the healthcare provider is a prescriber of medication.

7. A system, comprising;
  at least one memory operable to store computer-executable instructions; and at least one processor configured to access the at least one memory and execute the computer-executable instructions to:
  receive, from a healthcare provider computer associated with a healthcare provider, a first healthcare transaction, the first healthcare transaction comprising a medication identifier identifying a medication for a patient, a total group transaction number identifying a total number of healthcare transactions included in a first group, the total number of healthcare transactions being greater than one; a transaction number identifier; and a patient identifier identifying the patient to receive the respective medication identified in the first healthcare transaction;
  identify the total group transaction number and the transaction n umber identifier in the first healthcare transaction;
  compare the transaction number identifier to the total group transaction number to determine if the transaction number identifier equals the total group transaction number; in accordance with a determination that the transaction number identifier equals the total group transaction number, direct communication of the first healthcare transaction to a claims processor computer for adjudication;
  receive, from the claims processor computer, an adjudicated response to the first healthcare transaction, the adjudicated response comprising a first patient co-pay amount;
  identify the first patient co-pay amount in the adjudicated response for the first healthcare transaction;
  direct communication of a total patient pay amount at least partially based on the first patient co-pay amount to the healthcare provider computer;
  generate, automatically and without receiving a reversal request from the healthcare provider computer, a reversal transaction for the first healthcare transaction;
  direct communication of the first reversal transaction to the claims processor computer for adjudication; and
  receive, from the claims processor computer, an adjudicated response for the first reversal transaction.

8. The system of claim 7 wherein the at least one processor is further configured to access the at least one memory and execute the computer-executable instructions to delay transmission of the first healthcare transaction based on a determination that the respective transaction number identifier does not equal the total group transaction count.

9. The system of claim 7, wherein the total group transaction number is an integer greater than one.

10. The system of claim 9, wherein the at least one processor is further configured to access the at least one memory and execute the computer-executable instructions to receive and process a plurality of healthcare transactions including the first healthcare transaction equal in number to the total group transaction number.

11. The system of claim 7, wherein the at least one processor is further configured to access the at least one memory and execute the computer-executable instructions to:
  generate a total patient pay amount message comprising the total patient pay amount; and
  modify the adjudicated response by inserting the total patient pay amount message into the adjudicated response.

12. The system of claim 7, wherein the at least one processor is further configured to access the at least one memory and execute the computer-executable instructions to determine if the first healthcare transaction includes an indicator that signifies that multiple healthcare transactions are being submitted for the patient.

13. The system of claim 12, wherein the indicator comprises the total group transaction count in a predetermined field of the first healthcare transaction in an instance in which the first healthcare transaction includes the indicator.

14. A computer-implemented method, comprising: receiving, by a service provider computer associated with a service provider and comprising one or more processors from a healthcare provider computer associated with a healthcare provider, a first healthcare transaction, the first healthcare transaction comprising a medication identifier identifying a medication for a patient, a transaction number identifier, a total group transaction number identifying a total number of healthcare transactions, the total number of healthcare transactions being greater than one, and a patient identifier identifying the patient to receive the respective medication identified in the first healthcare transaction;
  in accordance with a determination that the transaction number identifier equals the total group transaction number transmitting, by the service provider computer, the first healthcare transaction to a claims processor computer for adjudication;
  receiving, by the service provider computer from the claims processor computer, an adjudicated response to the first healthcare transaction, the adjudicated response comprising a first patient co-pay amount;
  identifying, by the service provider computer, the first patient co-pay amount in the adjudicated response for the first healthcare transaction;
  transmitting, by the service provider computer, a total patient pay amount at least partially based on the first patient co-pay amount to the healthcare provider computer;
  generating, by the service provider computer automatically and without receiving a reversal request from the healthcare provider computer, a reversal transaction comprising a reversal transaction for the first healthcare transaction;
  transmitting, by the service provider computer, the reversal transaction to the claims processor computer for adjudication; and
  receiving, by the service provider computer and from the claims processor computer, an adjudicated response for the reversal transaction.

15. The computer-implemented method of claim 14, wherein the first healthcare transaction also comprises a total group transaction number identifying a number of healthcare transactions included in a first group wherein the total group transaction number is an integer greater than one.

16. The computer-implemented method of claim 15, further comprising receiving and processing a plurality of healthcare transactions including the first healthcare transaction equal in number to the total group transaction number.

17. The computer-implemented method of claim 16 further comprising calculating, by the service provider computer, the total patient pay amount by summing each respective patient co-pay amount in each respective adjudicated response for the plurality of healthcare transactions.

18. The computer-implemented method of claim 14, further comprising:
   generating, by the service provider computer, a total patient pay amount message comprising the total patient pay amount; and
   modifying, by the service provider computer, the adjudicated responses by inserting the total patient pay amount message into the adjudicated response.

19. The computer-implemented method of claim 14, further comprising determining, by the service provider computer, if the first healthcare transaction includes an indicator that signifies that multiple healthcare transactions are being submitted for the patient.

20. The computer-implemented method of claim 19, wherein the indicator comprises a total group transaction count in a predetermined field of the first healthcare transaction in an instance in which the first healthcare transaction includes the indicator.

\* \* \* \* \*

UNITED STATES PATENT AND TRADEMARK OFFICE
CERTIFICATE OF CORRECTION

PATENT NO. : 10,978,198 B1
APPLICATION NO. : 16/180915
DATED : April 13, 2021
INVENTOR(S) : Pinsonneault Page 1 of 1

It is certified that error appears in the above-identified patent and that said Letters Patent is hereby corrected as shown below:

In the Claims

<u>Column 31</u>,
Line 28, "n umber" should read --number--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*